United States Patent [19]

Shiozawa et al.

[11] Patent Number: 5,296,492
[45] Date of Patent: Mar. 22, 1994

[54] CERTAIN CHROMAN DERIVATIVES USEFUL FOR TREATING SYMPTOMS CAUSED BY CONTRACTION OF SMOOTH MUSCLES, CIRCULATORY DISEASES OR EPILEPSY

[75] Inventors: Akira Shiozawa, Omiya; Atsuro Inubushi, Tokyo; Kazuhisa Narita, Ageo; Yukihiro Sagawa, Yono; Makoto Hosono; Masashi Iida, both of Kitamoto, all of Japan

[73] Assignee: Nippon Kayaku Kabushiki Kaisha, Tokyo, Japan

[21] Appl. No.: 893,403

[22] Filed: Jun. 3, 1992

[30] Foreign Application Priority Data

Jun. 14, 1991 [JP] Japan .................. 03-169079

[51] Int. Cl.$^5$ .............. C07D 407/04; C07F 7/02; A61K 31/44; A61K 31/695
[52] U.S. Cl. .................. 514/337; 514/63; 546/14; 546/269
[58] Field of Search .............. 546/269, 14; 514/337, 514/63

[56] References Cited

U.S. PATENT DOCUMENTS 5,143,924 9/1992 Gericke et al. .............. 514/337

FOREIGN PATENT DOCUMENTS 0337179 10/1989 European Pat. Off. .......... 546/269
0410208 1/1991 European Pat. Off. .......... 544/238
0415065 3/1991 European Pat. Off. .......... 546/269
3923839 1/1991 Fed. Rep. of Germany ...... 546/269

OTHER PUBLICATIONS

Br. J. Pharmac. (1986), 88, 103-111; T. C. Hamilton, et al.: "Comparison of the Effects of BRL 34915 and Verapamil on . . . ".
Br. J. Pharmac. (1986) 89, 395-405; S. L. Allen, et al.; "Electrical and Mechanical Effects of BrL34915 in . . . ".

Primary Examiner—Alan L. Rotman
Attorney, Agent, or Firm—Nields & Lemack

[57] ABSTRACT

A chroman derivative represented by the following general formula [1]:

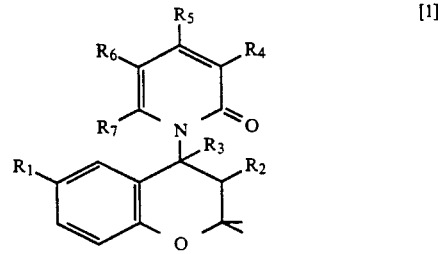

wherein $R_1$ represents cyano group, nitro group, halogenomethyl group or $-SO_2-X$ group (X represents lower alkyl group having 1-6 carbon atoms or aryl group); $R_2$ represents hydrogen atom or OA group (A represents hydrogen atom, nitro group, lower acyl group having 1-6 carbon atoms, arylcarbonyl group, lower alkylsulfonyl group having 1-6 carbon atoms, arylsulfonyl group, arylalkyl group, tetrahydropyranyl group, lower alkoxycarbonyl group having 1-6 carbon atoms, arylalkoxycarbonyl group or silyl derivative group); $R_3$ singly represents a hydrogen atom; or $R_3$ forms a bond jointly with $R_2$; and $R_4$, $R_5$, $R_6$ and $R_7$ each represent hydrogen atom, vinyl group, formyl group, $-Y-(OA)_n$ group (Y represents straight or branched chain alkylene group having 1-6 carbon atoms or lower alkenyl group having 1-6 carbon atoms, A is as defined above, and n represents an integer of 1-3.

The compound of this invention is expected to be effectively usable as an agent for treatment of various symptoms due to the contraction of smooth muscles, for treatment of the diseases of the circulatory system and for treatment of epilepsy.

12 Claims, No Drawings

CERTAIN CHROMAN DERIVATIVES USEFUL FOR TREATING SYMPTOMS CAUSED BY CONTRACTION OF SMOOTH MUSCLES, CIRCULATORY DISEASES OR EPILEPSY

FIELD OF THE INVENTION

This invention relates to novel chroman derivatives having a K ion channel opener activity.

BACKGROUND OF THE INVENTION

As compounds expectedly useful as an antihypertensive agent due to K ion channel opener activity, those represented by the following formula are known [U.S. Pat. No. 4,446,113; Br. J. Pharmac. (1986), 88, 103-111; Br. J. Pharmac. (1986), 89, 395-405]:

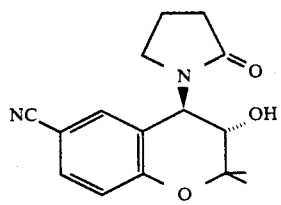

The purpose of the present invention is to develop new compounds having a K ion channel opener activity.

SUMMARY OF THE INVENTION

In view of the above, the present inventors have conducted various studies on a novel compound to find that the chroman derivatives represented by the following general formula [1] exhibit a K ion channel opener activity:

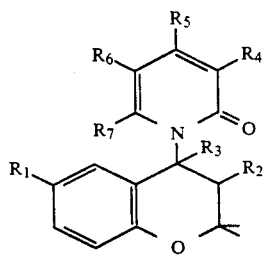

[1]

wherein R is cyano group, nitro group, halogenomethyl group or —$SO_2$—X group wherein X represents a lower alkyl group having 1-6 carbon atoms or an aryl group; $R_2$ is hydrogen atom or OA group, wherein A represents hydrogen atom, nitro group, lower acyl group having 1-6 carbon atoms, arylcarbonyl group, lower alkylsulfonyl group having 1-6 carbon atoms, arylsulfonyl group, arylalkyl group, tetrahydropyranyl group, lower alkoxycarbonyl group having 1-6 carbon atoms, arylalkoxycarbonyl group or silyl derivative group; $R_3$ singly represents a hydrogen atom; or $R_3$ forms a bond jointly with $R_2$; and $R_4$, $R_5$, $R_6$ and $R_7$ each represents hydrogen atom, vinyl group, formyl group, —Y—$(OA)_n$ group wherein Y is a straight or branched chain alkylene group having 1-6 carbon atoms or a lower alkenylene group having 1-6 carbon atoms, A is as defined above, and n is an integer of 1-3 provided that when n is 2 or greater, each OA groups are identical or independent of one another, or represent —CO—Z group wherein Z is hydrogen atom, lower alkyl group having 1-6 carbon atoms, aryl group, hydroxyl group or lower alkoxy group having 1-6 carbon atoms; provided that $R_4$, $R_5$, $R_6$ and $R_7$ are identical or independent of one another.

This invention has been accomplished on the basis of the finding mentioned above.

DETAILED DESCRIPTION OF THE INVENTION

In general formula [1], examples of the lower alkyl group having 1-6 carbon atoms include methyl, ethyl, n-propyl, isopropyl, n-butyl, s-butyl, t-butyl, n-pentyl, isopentyl, n-hexyl and the like. Examples of the aryl group include phenyl, o-, m- or p-tolyl, 1- and 2-naphthyl, o-, m- or p-methoxybenzyl group and the like. Examples of the lower acyl group having 1-6 carbon atoms include acetyl, n-propionyl, n-butyryl, isobutyryl, valeryl, pivaloyl and the like. Examples of the arylcarbonyl group include benzoyl, o-, m- or p-chlorobenzoyl and the like. Examples of the lower alkylsulfonyl group having 1-6 carbon atoms include methanesulfonyl, ethanesulfonyl, 2-butanesulfonyl and the like. Examples of the arylsulfonyl group include benzenesulfonyl, o-, m- or p-toluenesulfonyl and the like. Examples of the lower alkoxycarbonyl group having 1-6 carbon atoms include isopropyloxycarbonyl, n-amyloxycarbonyl, t-butoxycarbonyl and the like. Examples of the arylalkyloxycarbonyl group include benzyloxycarbonyl, p-methoxybenzyloxycarbonyl, o-chlorobenzyloxycarbonyl, 2,4-dichlorobenzyloxycarbonyl and the like. Examples of the silyl derivative include t-butyldimethylsilyl, t-butyldiphenylsilyl, diethylisopropylsilyl and the like. Examples of the lower alkoxy group having 1-6 carbon atoms include methoxy, ethoxy, n-propoxy, isopropoxy, n-butoxy, s-butoxy, t-butoxy, n-pentyloxy, isopentyloxy, n-hexyloxy and the like. Examples of halogen in halogenomethyl group includes fluorine, chlorine, bromine and iodine, its substitution number is 1 to 3, and trihalogenomethyl group is preferable. Examples of the trihalogenomethyl group include trifluoromethyl, trichloromethyl, tribromomethyl, triiodomethyl and the like.

Typical examples of the compound of this invention include the following:

1. tarns-3-hydroxy-6-cyano-3,4-dihydro-2,2-dimethyl-4-(1,2-dihydro-2-oxo-3-nitroxymetyl-1-pyridinyl)-2H-benzo[b]pyran,
2. trans-3-hydroxy-6-cyano-3,4-dihydro-2,2-dimethyl-4-(1,2-dihydro-2-oxo-4-nitroxymethyl-1-pyridinyl)-2H-benzo[b]pyran,
3. trans-3-hydroxy-6-cyano-3,4-dihydro-2,2-dimethyl-4-(1,2-dihydro-2-oxo-5-nitroxymethyl-1-pyridinyl)-2H-benzo[b]pyran,
4. trans-3-hydroxy-6-cyano-3,4-dihydro-2,2-dimethyl-4-(1,2-dihydro-2-oxo-6-nitroxymethyl-1-pyridinyl)-2H-benzo[b]pyran,
5. trans-3-hydroxy-6-cyano-3,4-dihydro-2,2-dimethyl-4-{1,2-dihydro-2-oxo-4-(1-nitroxyethyl)-1-pyridinyl}-2H-benzo[b]pyran,
6. trans-3-hydroxy-6-cyano-3,4-dihydro-2,2-dimethyl-4-{1,2-dihydro-2-oxo-4-(2-nitroxyethyl)-1-pyridinyl}-2H-benzo[b]pyran,
7. trans-3-hydroxy-6-cyano-3,4-dihydro-2,2-dimethyl-4-{1,2-dihydro-2-oxo-5-(1-nitroxyethyl)-1-pyridinyl}-2H-benzo[b]pyran,
8. trans-3-hydroxy-6-cyano-3,4-dihydro-2,2-dimethyl-4-{1,2-dihydro-2-oxo-5-(2-nitroxyethyl)-1-pyridinyl}-2H-benzo[b]pyran, 9. trans-3-hydroxy-6-cyano-3,4-dihydro-2,2-dimethyl-4-{1,2-dihydro-2-oxo-4-(2-nitroxypropyl)-1-pyridinyl}-2H-benzo[b]pyran,
10. trans-3-hydroxy-6-cyano-3,4-dihydro-2,2-dimethyl-4-{1,2-dihydro-2-oxo-4-(3-nitroxypropyl)-1-pyridinyl}-2H-benzo[b]pyran,
11. trans-3-hydroxy-6-cyano-3,4-dihydro-2,2-dimethyl-4-{1,2-dihydro-2-oxo-5-(2-nitroxypropyl)-1-pyridinyl}-2H-benzo[b]pyran,
12. trans-3-hydroxy-6-cyano-3,4-dihydro-2,2-dimethyl-4-{1,2-dihydro-2-oxo-5-(3-nitroxypropyl)-1-pyridinyl}-2H-benzo[b]pyran,
13. trans-3-hydroxy-6-cyano-3,4-dihydro-2,2-dimethyl-4-{1,2-dihydro-2-oxo-4-(3-nitroxybutyl)-1-pyridinyl}-2H-benzo[b]pyran,
14. trans-3-hydroxy-6-cyano-3,4-dihydro-2,2-dimethyl-4-{1,2-dihydro-2-oxo-4-(4-nitroxybutyl)-1-pyridinyl}-2H-benzo[b]pyran,
15. trans-3-hydroxy-6-cyano-3,4-dihydro-2,2-dimethyl-4-{1,2-dihydro-2-oxo-5-(3-nitroxybutyl)-1-pyridinyl}-2H-benzo[b]pyran,
16. trans-3-hydroxy-6-cyano-3,4-dihydro-2,2-dimethyl-4-{1,2-dihydro-2-oxo-5-(4-nitroxybutyl)-1-pyridinyl}-2H-benzo[b]pyran,
17. trans-3-hydroxy-6-cyano-3,4-dihydro-2,2-dimethyl-4-(1,2-dihydro-2-oxo-3,4-bisnitroxymethyl-1-pyridinyl)-2H-benzo[b]pyran,
18. trans-3-hydroxy-6-cyano-3,4-dihydro-2,2-dimethyl-4-(1,2-dihydro-2-oxo-3,5-bisnitroxymethyl-1-pyridinyl)-2H-benzo[b]pyran,
19. trans-3-hydroxy-6-cyano-3,4-dihydro-2,2-dimethyl-4-(1,2-dihydro-2-oxo-4,5-bisnitroxymethyl-1-pyridinyl)-2H-benzo[b]pyran,
20. trans-3-hydroxy-6-cyano-3,4-dihydro-2,2-dimethyl-4-{1,2-dihydro-2-oxo-4-(1,2-dinitroxyethyl)-1-pyridinyl}-2H-benzo[b]pyran,
21. trans-3-hydroxy-6-cyano-3,4-dihydro-2,2-dimethyl-4-{1,2-dihydro-2-oxo-5-(1,2-dinitroxyethyl)-1-pyridinyl}2H-benzo[b]pyran,
22. trans-3-hydroxy-6-cyano-3,4-dihydro-2,2-dimethyl-4-{1,2-dihydro-2-oxo-4-(1,2-dinitroxypropyl)-1-pyridinyl}-2H-benzo[b]pyran,
23. trans-3-hydroxy-6-cyano-3,4-dihydro-2,2-dimethyl-4-{1,2-dihydro-2-oxo-5-(1,2-dinitroxypropyl)-1-pyridinyl}-2H-benzo[b]pyran,
24. trans-3-hydroxy-6-cyano-3,4-dihydro-2,2-dimethyl-4-{1,2-dihydro-2-oxo-4-(1,3-dinitroxypropyl)-1-pyridinyl}-2H-benzo[b]pyran,
25. trans-3-hydroxy-6-cyano-3,4-dihydro-2,2-dimethyl-4-{1,2-dihydro-2-oxo-5-(1,3-dinitroxypropyl)-1-pyridinyl}-2H-benzo[b]pyran,
26. trans-3-hydroxy-6-cyano-3,4-dihydro-2,2-dimethyl-4-{1,2-dihydro-2-oxo-4-(2,3-dinitroxypropyl)-1-pyridinyl}-2H-benzo[b]pyran,
27. trans-3-hydroxy-6-cyano-3,4-dihydro-2,2-dimethyl-4-{1,2-dihydro-2-oxo-5-(2,3-dinitroxypropyl)-1-pyridinyl}-2H-benzo[b]pyran,
28. trans-3-hydroxy-6-cyano-3,4-dihydro-2,2-dimethyl-4-{1,2-dihydro-2-oxo-4-(1,3-dinitroxybutyl)-1-pyridinyl}-2H-benzo[b]pyran,
29. trans-3-hydroxy-6-cyano-3,4-dihydro-2,2-dimethyl-4-{1,2-dihydro-2-oxo-5-(1,3-dinitroxybutyl)-1-pyridinyl}-2H-benzo[b]pyran,
30 trans-3-hydroxy-6-cyano-3,4-dihydro-2,2-dimethyl-4-(1,2-dihydro-2-oxo-4-(1,4-dinitroxybutyl)-1-pyridinyl}-2H-benzo[b]pyran,
31 trans-3-hydroxy-6-cyano-3,4-dihydro-2,2-dimethyl-4-{1,2-dihydro-2-oxo-5-(1,4-dinitroxybutyl)-1-pyridinyl}-2H-benzo[b]pyran,
32. trans-3-hydroxy-6-cyano-3,4-dihydro-2,2-dimethyl-4-{1,2-dihydro-2-oxo-4-(2,3-dinitroxybutyl)-1-pyridinyl}-2H-benzo[b]pyran,
33. trans-3-hydroxy-6-cyano-3,4-dihydro-2,2-dimethyl-4-{1,2-dihydro-2-oxo-5-(2,3-dinitroxybutyl)-1-pyridinyl}-2H-benzo[b]pyran,
34 trans-3-hydroxy-6-cyano-3,4-dihydro-2,2-dimethyl-4-{1,2-dihydro-2-oxo-4-(2,4-dinitroxybutyl)-1-pyridinyl}-2H-benzo[b]pyran,
35. trans-3-hydroxy-6-cyano-3,4-dihydro-2,2-dimethyl-4-{1,2-dihydro-2-oxo-5-(2,4-dinitroxybutyl)-1-pyridinyl}-2H-benzo[b]pyran,
36. trans-3-hydroxy-6-cyano-3,4-dihydro-2,2-dimethyl-4-{1,2-dihydro-2-oxo-4-(3,4-dinitroxybutyl)-1-pyridinyl}-2H-benzo[b]pyran,
37. trans-3-hydroxy-6-cyano-3,4-dihydro-2,2-dimethyl-4-{1,2-dihydro-2-oxo-5-(3,4-dinitroxybutyl)-1-pyridinyl}-2H-benzo[b]pyran,
38. trans-3-nitroxy-6-cyano-3,4-dihydro-2,2-dimethyl-4-(1,2-dihydro-2-oxo-4-nitroxymethyl-1-pyridinyl)-2H-benzo[b]pyran,
39. trans-3-nitroxy-6-cyano-3,4-dihydro-2,2-dimethyl-4-(1,2-dihydro-2-oxo-5-nitroxymethyl-1-pyridinyl)-2H-benzo[b]pyran,
40. trans-3-nitroxy-6-cyano-3,4-dihydro-2,2-dimethyl-4-{1,2-dihydro-2-oxo-4-(1-nitroxyethyl)-1-pyridinyl}-2H-benzo[b]pyran,
41. trans-3-nitroxy-6-cyano-3,4-dihydro-2,2-dimethyl-4-{1,2-dihydro-2-oxo-4-(2-nitroxyethyl)-1-pyridinyl}-2H-benzo[b]pyran,
42. trans-3-nitroxy-6-cyano-3,4-dihydro-2,2-dimethyl-4-(1,2-dihydro-2-oxo-4,5-bisnitroxymethyl-1-pyridinyl)-2H-benzo[b]pyran,
43. trans-3-nitroxy-6-cyano-3,4-dihydro-2,2-dimethyl-4-{1,2-dihydro-2-oxo-4-(1,4-dinitroxybutyl)-1-pyridinyl} -2H-benzo[b]pyran,
44 trans-3-acetoxy-6-cyano-3,4-dihydro-2,2-dimethyl-4-(1,2-dihydro-2-oxo-4-nitroxymethyl-1-pyridinyl)-2H-benzo[b]pyran,
45. trans-3-acetoxy-6-cyano-3,4-dihydro-2,2-dimethyl-4-(1,2-dihydro-2-oxo-5-nitroxymethyl-1-pyridinyl)-2H-benzo[b]pyran,
46 trans-3-acetoxy-6-cyano-3,4-dihydro-2,2-dimethyl-4-{1,2-dihydro-2-oxo-4-(1-nitroxyethyl)-1-pyridinyl}-2H-benzo[b]pyran,
47. trans-3-acetoxy-6-cyano-3,4-dihydro-2,2-dimethyl-4-{1,2-dihydro-2-oxo-4-(2-nitroxyethyl)-1-pyridinyl}-2H-benzo[b]pyran,
48. trans-3-acetoxy-6-cyano-3,4-dihydro-2,2-dimethyl-4-(1,2-dihydro-2-oxo-4,5-bisnitroxymethyl-1-pyridinyl)-2H-benzo[b]pyran,
49. trans-3-acetoxy-6-cyano-3,4-dihydro-2,2-dimethyl-4-{1,2-dihydro-2-oxo-4-(1,4-dinitroxybutyl)-1-pyridinyl}-2H-benzo[b]pyran,
50. trans-3-hydroxy-6-trifluoromethyl-3,4-dihydro-2,2-dimethyl-4-(1,2-dihydro-2-oxo-4-nitroxymethyl-1-pyridinyl)-2H-benzo[b]pyran,
51. trans-3-hydroxy-6-trifluoromethyl-3,4-dihydro-2,2-dimethyl-4-(1,2-dihydro-2-oxo-5-nitroxymethyl-1-pyridinyl)-2H-benzo[b]pyran,
52. trans-3-hydroxy-6-trifluoromethyl-3,4-dihydro-2,2-dimethyl-4-{1,2-dihydro-2-oxo-4-(1-nitroxyethyl)-1-pyridinyl}-2H-benzo[b]pyran, 53. trans-3-hydroxy-6-trifluoromethyl-3,4-dihydro-2,2-dimethyl-4-{1,2-dihydro-2-oxo-4-(2-nitroxyethyl)-1-pyridinyl}-2H-benzo[b]pyran,
54. trans-3-hydroxy-6-trifluoromethyl-3,4-dihydro-2,2-dimethyl-4-(1,2-dihydro-2-oxo-4,5-bisnitroxymethyl-1-pyridinyl)-2H-benzo[b]pyran,
55. trans-3-hydroxy-6-trifluoromethyl-3,4-dihydro-2,2-dimethyl-4-{1,2-dihydro-2-oxo-4-(1,4-dinitroxybutyl)-1-pyridinyl}-2H-benzo[b]pyran,
56. trans-3-nitroxy-6-trifluoromethyl-3,4-dihydro-2,2-dimethyl-4-(1,2-dihydro-2-oxo-4-nitroxymethyl-1-pyridinyl)-2H-benzo[b]pyran,
57. trans-3-nitroxy-6-trifluoromethyl-3,4-dihydro-2,2-dimethyl-4-(1,2-dihydro-2-oxo-5-nitroxymethyl-1-pyridinyl)-2H-benzo[b]pyran,
58. trans-3-nitroxy-6-trifluoromethyl-3,4-dihydro-2,2-dimethyl-4-{1,2-dihydro-2-oxo-4-(1-nitroxyethyl)-1-pyridinyl}-2H-benzo[b]pyran,
59. trans-3-nitroxy-6-trifluoromethyl-3,4-dihydro-2,2-dimethyl-4-{1,2-dihydro-2-oxo-4-(2-nitroxyethyl)-1-pyridinyl}-2H-benzo[b]pyran,
60. trans-3-nitroxy-6-trifluoromethyl-3,4-dihydro-2,2-dimethyl-4-(1,2-dihydro-2-oxo-4,5-bisnitroxymethyl-1-pyridinyl)-2H-benzo[b]pyran,
61. trans-3-nitroxy-6-trifluoromethyl-3,4-dihydro-2,2-dimethyl-4-{1,2-dihydro-2-oxo-4-(1,4-dinitroxybutyl)-1-pyridinyl}-2H-benzo[b]pyran,
62 trans-3-acetoxy-6-trifluoromethyl-3,4-dihydro- 2,2-dimethyl-4-(1,2-dihydro-2-oxo-4-nitroxymethyl-1-pyridinyl)-2H-benzo[b]pyran,
63. trans-3-acetoxy-6-trifluoromethyl-3,4-dihydro-2,2-dimethyl-4-(1,2-dihydro-2-oxo-5-nitroxymethyl-1-pyridinyl)-2H-benzo[b]pyran,
64. trans-3-acetoxy-6-trifluoromethyl-3,4-dihydro-2,2-dimethyl-4-{1,2-dihydro-2-oxo-4-(1-nitroxyethyl)-1-pyridinyl}-2H-benzo[b]pyran,
65. trans-3-acetoxy-6-trifluoromethyl-3,4-dihydro-2,2-dimethyl-4-{1,2-dihydro-2-oxo-4-(2-nitroxyethyl)-1-pyridinyl}-2H-benzo[b]pyran,
66. trans-3-acetoxy-6-trifluoromethyl-3,4-dihydro-2,2-dimethyl-4-(1,2-dihydro-2-oxo-4,5-bisnitroxymethyl-1-pyridinyl)-2H-benzo[b]pyran,
67. trans-3-acetoxy-6-trifluoromethyl-3,4-dihydro-2,2-dimethyl-4-{1,2-dihydro-2-oxo-4-(1,4-dinitroxybutyl)-1-pyridinyl}-2H-benzo[b]pyran,
68. 6-cyano-2,2-dimethyl-4-(1,2-dihydro-2-oxo-3-nitroxymethyl-1-pyridinyl)-2H-benzo[b]pyran,
69. 6-cyano-2,2-dimethyl-4-(1,2-dihydro-2-oxo-4-nitroxymethyl-1-pyridinyl)-2H-benzo[b]pyran,
70. 6-cyano-2,2-dimethyl-4-(1,2-dihydro-2-oxo-5-nitroxymethyl-1-pyridinyl)-2H-benzo[b]pyran,
71. 6-cyano-2,2-dimethyl-4-(1,2-dihydro-2-oxo-6-nitroxymethyl-1-pyridinyl)-2H-benzo[b]pyran,
72. 6-cyano-2,2-dimethyl-4-{1,2-dihydro-2-oxo-4-(1-nitroxyethyl)-1-pyridinyl}-2H-benzo[b]pyran,
73. 6-cyano-2,2-dimethyl-4-{1,2-dihydro-2-oxo-4-(2-nitroxyethyl)- 1-pyridinyl}-2H-benzo[b]pyran,
74. 6-cyano-2,2-dimethyl-4-{1,2-dihydro-2-oxo-5-(1-nitroxyethyl)-1-pyridinyl}-2H-benzo[b]pyran,
75. 6-cyano-2,2-dimethyl-4-{1,2-dihydro-2-oxo-5-(2-nitroxyethyl)-1-pyridinyl}-2H-benzo[b]pyran,
76 6-cyano-2,2-dimethyl-4-{1,2-dihydro-2-oxo-4-(2-nitroxypropyl)-1-pyridinyl}-2H-benzo[b]pyran,
77. 6-cyano-2,2-dimethyl-4-{1,2-dihydro-2-oxo-4-(3-nitroxypropyl)-1-pyridinyl}-2H-benzo[b]pyran,
78. 6-cyano-2,2-dimethyl-4-{1,2-dihydro-2-oxo-5-(2-nitroxypropyl)-1-pyridinyl}-2H-benzo[b]pyran,
79. 6-cyano-2,2-dimethyl-4-{1,2-dihydro-2-oxo-5-(3-nitroxypropyl)-1-pyridinyl}-2H-benzo[b]pyran,
80. 6-cyano-2,2-dimethyl-4-{1,2-dihydro-2-oxo-4-(3-nitroxybutyl)-1-pyridinyl}-2H-benzo[b]pyran,
81 6-cyano-2,2-dimethyl-4-{1,2-dihydro-2-oxo-4-(4-nitroxybutyl)-1-pyridinyl}-2H-benzo[b]pyran,
82. 6-cyano-2,2-dimethyl-4-{1,2-dihydro-2-oxo-5-(3-nitroxybutyl)-1-pyridinyl}-2H-benzo[b]pyran,
83. 6-cyano-2,2-dimethyl-4-{1,2-dihydro-2-oxo-5-(4-nitroxybutyl)-1-pyridinyl}-2H-benzo[b]pyran,
84. 6-cyano-2,2-dimethyl-4-(1,2-dihydro-2-oxo-3,4-bis-nitroxymethyl-1-pyridinyl)-2H-benzo[b]pyran,
85. 6-cyano-2,2-dimethyl-4-(1,2-dihydro-2-oxo-3,5-bis-nitroxymethyl-1-pyridinyl)-2H-benzo[b]pyran,
86. 6-cyano-2,2-dimethyl-4-(1,2-dihydro-2-oxo-4,5-bis-nitroxymethyl-1-pyridinyl)-2H-benzo[b]pyran,
87. 6-cyano-2,2-dimethyl-4-{1,2-dihydro-2-oxo-4-( 1,2-dinitroxyethyl)-1-pyridinyl}-2H-benzo[b]pyran,
88. 6-cyano-2,2-dimethyl-4-{1,2-dihydro-2-oxo-5-(1,2-dinitroxypropyl)-1-pyridinyl}-2H-benzo[b]-pyran,
89. 6-cyano-2,2-dimethyl-4-{1,2-dihydro-2-oxo-4-(1,2-dinitroxypropyl)-1-pyridinyl}-2H-benzo[b]pyran,
90. 6-cyano-2,2-dimethyl-4-{1,2-dihydro-2-oxo-5-(1,2-dinitroxypropyl)-1-pyridinyl}-2H-benzo[b]pyran,
91 6-cyano-2,2-dimethyl-4-{1,2-dihydro-2-oxo-4-(1,3-dinitroxypropyl)-1-pyridinyl}-2H-benzo[b]pyran,
92. 6-cyano-2,2-dimethyl-4-{1,2-dihydro-2-oxo-5-(1,3-dinitroxypropyl)-1-pyridinyl}-2H-benzo[b]pyran,
93. 6-cyano-2,2-dimethyl-4-{1,2-dihydro-2-oxo-4-(2,3-dinitroxypropyl)-1-pyridinyl}-2H-benzo[b]pyran,
94. 6-cyano-2,2-dimethyl-4-{1,2-dihydro-2-oxo-5-(2,3-dinitroxypropyl)-1-pyridinyl}-2H-benzo[b]pyran,
95. 6-cyano-2,2-dimethyl-4-{1,2-dihydro-2-oxo-4-(1,3-dinitroxybutyl)-1-pyridinyl}-2H-benzo[b]pyran,
96. 6-cyano-2,2-dimethyl-4-{1,2-dihydro-2-oxo-5-(1,3-dinitroxybutyl)-1-pyridinyl}-2H-benzo[b]pyran,
97 6-cyano-2,2-dimethyl-4-{1,2-dihydro-2-oxo-4-(1,4-dinitroxybutyl)-1-pyridinyl}-2H-benzo[b]pyran,
98. 6-cyano-2,2-dimethyl-4-{1,2-dihydro-2-oxo-5-(1,4-dinitroxybutyl)-1-pyridinyl}-2H-benzo[b]pyran,
99. 6-cyano-2,2-dimethyl-4-{1,2-dihydro-2-oxo-4-(2,3-dinitroxybutyl)-1-pyridinyl}-2H-benzo[b]pyran,
100 6-cyano-2,2-dimethyl-4-{1,2-dihydro-2-oxo-5-(2,3-dinitroxybutyl)-1-pyridinyl}-2H-benzo[b]pyran,
101. 6-cyano-2,2-dimethyl-4-{1,2-dihydro-2-oxo-4-( 2,4-dinitroxybutyl)-1-pyridinyl}-2H-benzo[b]pyran,
102. 6-cyano-2,2-dimethyl-4-{1,2-dihydro-2-oxo-5-(2,4-dinitroxybutyl)-1-pyridinyl}-2H-benzo[b]pyran,
103. 6-cyano-2,2-dimethyl-4-{1,2-dihydro-2-oxo-4-(3,4-dinitroxybutyl)-1-pyridinyl}-2H-benzo[b]pyran,
104. 6-cyano-2,2-dimethyl-4-{1,2-dihydro-2-oxo-5-(3,4-dinitroxybutyl)-1-pyridinyl}-2H-benzo[b]pyran,
105. 6-trifluoromethyl-2,2-dimethyl-4-(1,2-dihydro-2-oxo-4-nitroxymethyl-1-pyridinyl)-2H-benzo[b]pyran,
106. 6-trifluoromethyl-2,2-dimethyl-4-(1,2-dihydro-2-oxo-5-nitroxymethyl-1-pyridinyl)-2H-benzo[b]pyran,
107. 6-trifluoromethyl-2,2-dimethyl-4-{1,2-dihydro-2-oxo-4-(1-nitroxyethyl)-1-pyridinyl}-2H-benzo[b]pyran,
108. 6-trifluoromethyl-2,2-dimethyl-4-{1,2-dihydro-2-oxo-4-(2-nitroxyethyl)-1-pyridinyl}-2H-benzo[b]pyran,
109. 6-trifluoromethyl-2,2-dimethyl-4-(1,2-dihydro-2-oxo-4,5-bisnitroxymethyl-1-pyridinyl)-2H-benzo[b]-pyran,
110. 6-trifluoromethyl-2,2-dimethyl-4-{1,2-dihydro-2-oxo-4-(1,4-dinitroxybutyl)-1-pyridinyl}-2H-benzo[b]-pyran, 111. trans-3-hydroxy-6-cyano-3,4-dihydro-2,2-dimethyl-4-(1,2-dihydro-2-oxo-4-hydroxymethyl-1-pyridinyl)-2H-benzo[b]pyran,
112. trans-3-hydroxy-6-cyano-3,4-dihydro-2,2-dimethyl-4-(1,2-dihydro-2-oxo-5-hydroxymethyl-1-pyridinyl)-2H-benzo[b]pyran,
113. trans-3-hydroxy-6-cyano-3,4-dihydro-2,2-dimethyl-4-{1,2-dihydro-2-oxo-4-(1-hydroxyethyl)-1-pyridinyl} -2H-benzo[b]pyran,
114 trans-3-hydroxy-6-cyano-3,4-dihydro-2,2-dimethyl-4-{1,2-dihydro-2-oxo-4-(2-hydroxyethyl)-1-pyridinyl}-2H-benzo[b]pyran,
115. trans-3-hydroxy-6-cyano-3,4-dihydro-2,2-dimethyl-4-(1,2-dihydro-2-oxo-4,5-bishydroxymethyl-1-pyridinyl)-2H-benzo[b]pyran,
116. trans-3-hydroxy-6-cyano-3,4-dihydro-2,2-dimethyl-4-{1,2-dihydro-2-oxo-4-(1,4-dihydroxybutyl)-1-pyridinyl}-2H-benzo[b]pyran,
117. trans-3-acetoxy-6-cyano-3,4-dihydro-2,2-dimethyl-4-(1,2-dihydro-2-oxo-4-hydroxymethyl-1-pyridinyl)-2H-benzo[b]pyran,
118. trans-3-acetoxy-6-cyano-3,4-dihydro-2,2-dimethyl-4-(1,2-dihydro-2-oxo-5-hydroxymethyl-1-pyridinyl)-2H-benzo[b]pyran,
119. trans-3-acetoxy-6-cyano-3,4-dihydro-2,2-dimethyl-4-{1,2-dihydro-2-oxo-4-(1-hydroxyethyl)-1-pyridinyl}-2H-benzo[b]pyran,
120. trans-3-acetoxy-6-cyano-3,4-dihydro-2,2-dimethyl-4-{1,2-dihydro-2-oxo-4-(2-hydroxyethyl)-1-pyridinyl}-2H-benzo[b]pyran,
121. trans-3-acetoxy-6-cyano-3,4-dihydro-2,2-dimethyl-4-(1,2-dihydro-2-oxo-4,5-bishydydroxymethyl-1-pyridinyl)-2H-benzo[b]pyran,
122. trans-3-acetoxy-6-cyano-3,4-dihydro-2,2-dimethyl-4-{1,2-dihydro-2-oxo-4-(1,4-dihydroxybutyl)-1-pyridinyl}-2H-benzo[b]pyran,
123. trans-3-hydroxy-6-cyano-3,4-dihydro-2,2-dimethyl-4-(1,2-dihydro-2-oxo-3-t-butyldimethylsilyloxymethyl-1-pyridinyl)-2H-benzo[b]pyran,
124. trans-3-hydroxy-6-cyano-3,4-dihydro-2,2-dimethyl-4-(1,2-dihydro-2-oxo-4-t-butyldimethylsilyloxymethyl-1-pyridinyl)-2H-benzo[b]pyran,
125. trans-3-hydroxy-6-cyano-3,4-dihydro-2,2-dimethyl-4-(1,2-dihydro-2-oxo-5-t-butyldimethylsilyloxymethyl-1-pyridinyl)-2H-benzo[b]pyran,
126. trans-3-hydroxy-6-cyano-3,4-dihydro-2,2-dimethyl-4-{1,2-dihydro-2-oxo-4-(1-t-butyldimethylsilyloxyethyl)-1-pyridinyl}-2H-benzo[b]pyran,
127. trans-3-hydroxy-6-cyano-3,4-dihydro-2,2-dimethyl-4-{1,2-dihydro-2-oxo-4-(2-t-butyldimethylsilyloxyethyl)-1-pyridinyl}-2H-benzo[b]pyran,
128. trans-3-hydroxy-6-cyano-3,4-dihydro-2,2-dimethyl-4-(1,2-dihydro-2-oxo-4,5-bis-t-butyldimethylsilyloxymethyl-1-pyridinyl)-2H-benzo[b]pyran,
129. trans-3-hydroxy-6-cyano-3,4-dihydro-2,2-dimethyl-4-{1,2-dihydro-2-oxo-4-(1,4-di-t-butyldimethylsilyloxybutyl)-1-pyridinyl}-2H-benzo[b]pyran,
130 trans-3-acetoxy-6-cyano-3,4-dihydro-2,2-dimethyl-4-(1,2-dihydro-2-oxo-4-t-butyldimethylsilyloxymethyl-1-pyridinyl-2H-benzo[b]pyran,
131. trans-3-acetoxy-6-cyano-3,4-dihydro-2,2-dimethyl-4-(1,2-dihydro-2-oxo-5-t-butyldimethylsilyloxymethyl-1-pyridinyl)-2H-benzo[b]pyran,
132. trans-3-acetoxy-6-cyano-3,4-dihydro-2,2-dimethyl-4-{1,2-dihydro-2-oxo-4-(1-t-butyldimethylsilyloxyethyl)-1-pyridinyl}-2H-benzo[b]pyran,
133. trans-3-acetoxy-6-cyano-3,4-dihydro-2,2-dimethyl-4-{1,2-dihydro-2-oxo-4-(2-t-butyldimethylsilyloxyethyl)-1-pyridinyl}-2H-benzo[b]pyran,
134. trans-3-acetoxy-6-cyano-3,4-dihydro-2,2-dimethyl-4-(1,2-dihydro-2-oxo-4,5-bis-t-butyldimethylsilyloxymethyl-1-pyridinyl)-2H-benzo[b]pyran,
135. trans-3-acetoxy-6-cyano-3,4-dihydro-2,2-dimethyl-4-{1,2-dihydro-2-oxo-4-(1,4-di-t-butyldimethylsilyloxybutyl)-1-pyridinyl}-2H-benzo[b]pyran,
136. trans-3-hydroxy-6-cyano-3,4-dihydro-2,2-dimethyl-4-(1,2-dihydro-2-oxo-4-benzyloxymethyl-1-pyridinyl)-2H-benzo[b]pyran,
137. trans-3-hydroxy-6-cyano-3,4-dihydro-2,2-dimethyl-4-(1,2-dihydro-2-oxo-5-benzyloxymethyl-1-pyridinyl)-2H-benzo[b]pyran,
138. trans-3-hydroxy-6-cyano-3,4-dihydro-2,2-dimethyl-4-{1,2-dihydro-2-oxo-4-(1-benzyloxyethyl)-1-pyridinyl}-2H-benzo[b]pyran,
139. trans-3-hydroxy-6-cyano-3,4-dihydro-2,2-dimethyl-4-{1,2-dihydro-2-oxo-4-(2-benzyloxyethyl)-1-pyridinyl}-2H-benzo[b]pyran,
140. trans-3-hydroxy-6-cyano-3,4-dihydro-2,2-dimethyl-4-(1,2-dihydro-2-oxo-4,5-bisbenzyloxymethyl-1-pyridinyl)-2H-benzo[b]pyran,
141. trans-3-hydroxy-6-cyano-3,4-dihydro-2,2-dimethyl- 4-{1,2-dihydro-2-oxo-4-(1,4-dibenzyloxybutyl)-1-pyridinyl}-2H-benzo[b]pyran,
142. trans-3-acetoxy-6-cyano-3,4-dihydro-2,2-dimethyl-4-(1,2-dihydro-2-oxo-4-benzyloxymethyl-1-pyridinyl)-2H-benzo[b]pyran,
143. trans-3-acetoxy-6-cyano-3,4-dihydro-2,2-dimethyl-4-(1,2-dihydro-2-oxo-5-benzyloxymethyl-1-pyridinyl)-2H-benzo[b]pyran,
144. trans-3-acetoxy-6-cyano-3,4-dihydro-2,2-dimethyl-4-{1,2-dihydro-2-oxo-4-(1-benzyloxyethyl)-1-pyridinyl}-2H-benzo[b]pyran,
145. trans-3-acetoxy-6-cyano-3,4-dihydro-2,2-dimethyl-4-{1,2-dihydro-2-oxo-4-(2-benzyloxyethyl)-1-pyridinyl}-2H-benzo[b]pyran,
146. trans-3-acetoxy-6-cyano-3,4-dihydro-2,2-dimethyl-4-(1,2-dihydro-2-oxo-4,5-bisbenzyloxymethyl-1-pyridinyl)-2H-benzo[b]pyran,
147. trans-3-acetoxy-6-cyano-3,4-dihydro-2,2-dimethyl-4-{1,2-dihydro-2-oxo-4-(1,4-dibenzyloxybutyl)-1-pyridinyl}-2H-benzo[b]pyran,
148. trans-3-hydroxy-6-cyano-3,4-dihydro-2,2-dimethyl-4-(1,2-dihydro-2-oxo-4-methanesulfonyloxymethyl-1-pyridinyl)-2H-benzo[b]pyran,
149. trans-3-hydroxy-6-cyano-3,4-dihydro-2,2-dimethyl-4-(1,2-dihydro-2-oxo-5-methanesulfonyloxymethyl-1-pyridinyl)-2H-benzo[b]pyran,
150. trans-3-hydroxy-6-cyano-3,4-dihydro-2,2-dimethyl-4-{1,2-dihydro-2-oxo-4-(1-methanesulfonyloxy)-ethyl- 1-pyridinyl}-2H-benzo[b]pyran,
151. trans-3-hydroxy-6-cyano-3,4-dihydro-2,2-dimethyl-4-{1,2-dihydro-2-oxo-4-(2-methanesulfonyloxy)-ethyl-1-pyridinyl}-2H-benzo[b]pyran,
152. trans-3-hydroxy-6-cyano-3,4-dihydro-2,2-dimethyl-4-(1,2-dihydro-2-oxo-4,5-bismethanesulfonyloxymethyl-1-pyridinyl)-2H-benzo[b]pyran,
153. trans-3-hydroxy-6-cyano-3,4-dihydro-2,2-dimethyl-4-{1,2-dihydro-2-oxo-4-(1,4-dimethanesulfonyloxybutyl)-1-pyridinyl}-2H-benzo[b]pyran,
154. trans-3-acetoxy-6-cyano-3,4-dihydro-2,2-dimethyl-4-(1,2-dihydro-2-oxo-4-methanesulfonyloxymethyl-1-pyridinyl)-2H-benzo[b]pyran, 155. tans-3-acetoxy-6-cyane-3,4-dihydro-2,2-dimethyl-4-(1,2-dihydro-2-oxo-5-methanesulfonyloxymethyl-1-pyridinyl)-2H-benzo[b]pyran, 156. trans-3-acetoxy-6-cyano-3,4-dihydro-2,2-dimethyl-4-{1,2-dihydro-2-oxo-4-(1-methanesulfonyloxyethyl)-1-pyridinyl}-2H-benzo[b]pyran, 157. trans-3-acetoxy-6-cyano-3,4-dihydro-2,2-dimethyl-4-{1,2-dihydro-2-oxo-4-(2-methanesulfonyloxyethyl)-1-pyridinyl}-2H-benzo[b]pyran, 158. trans-3-acetoxy-6-cyano-3,4-dihydro-2,2-dimethyl-4-(1,2-dihydro-2-oxo-4,5-bismethanesulfonyloxymethyl-1-pyridinyl)-2H-benzo[b]pyran, 159. trans-3-acetoxy-6-cyano-3,4-dihydro-2,2-dimethyl-4-{1,2-dihydro-2-oxo-4-(1,4-dimethanesulfonyloxybutyl)-1-pyridinyl}-2H-benzo[b]pyran, 160. 6-cyano-2,2-dimethyl-4-(1,2-dihydro-2-oxo-3-hydroxymethyl-1-pyridinyl)-2H-benzo[b]pyran, 161. 6-cyano-2,2-dimethyl-4-(1,2-dihydro-2-oxo-4-hydroxymethyl-1-pyridinyl)-2H-benzo[b]pyran, 162. 6-cyano-2,2-dimethyl-4-(1,2-dihydro-2-oxo-5-hydroxymethyl-1-pyridinyl)-2H-benzo[b]pyran, 163. 6-cyano-2,2-dimethyl-4-{1,2-dihydro-2-oxo-4-(1-hydroxyethyl)-1-pyridinyl}-2H-benzo[b]pyran, 164. 6-cyano-2,2-dimethyl-4-{1,2-dihydro-2-oxo-4-(2-hydroxyethyl)-1-pyridinyl}-2H-benzo[b]pyran, 165. 6-cyano-2,2-dimethyl-4-(1,2-dihydro-2-oxo-4,5-bishydroxymethyl-1-pyridinyl)-2H-benzo[b]pyran, 166. 6-cyano-2,2-dimethyl-4-{1,2-dihydro-2-oxo-4-(1,4-dihydroxybutyl)-1-pyridinyl}-2H-benzo[b]pyran, 167. 6-cyano-2,2-dimethyl-4-(1,2-dihydro-2-oxo-3-t-butyldimethylsilyloxymethyl-1-pyridinyl)-2H-benzo[b]pyran, 168. 6-cyano-2,2-dimethyl-4-(1,2-dihydro-2-oxo-4-t-butyldimethylsilyloxymethyl-1-pyridinyl)-2H-benzo[b]pyran, 169. 6-cyano-2,2-dimethyl-4-(1,2-dihydro-2-oxo-5-t-butyldimethylsilyloxymethyl-1-pyridinyl)-2H-benzo[b]pyran, 170. 6-cyano-2,2-dimethyl-4-{1,2-dihydro-2-oxo-4-(1-t-butyldimethylsilyloxyethyl)-1-pyridinyl}-2H-benzo[b]pyran, 171. 6-cyano-2,2-dimethyl-4-{1,2-dihydro-2-oxo-4-(2-t-butyldimethylsilyloxyethyl)-1-pyridinyl}-2H-benzo[b]pyran, 172. 6-cyano-2,2-dimethyl-4-(1,2-dihydro-2-oxo-4,5-bis-t-butyldimethylsilyloxymethyl-1-pyridinyl)-2H-benzo[b]pyran, 173. 6-cyano-2,2-dimethyl-4-{1,2-dihydro-2-oxo-4-(1,4-di-butyldimethylsilyloxybutyl)-1-pyridinyl}-2H-benzo[b]pyran, 174. 6-cyano-2,2-dimethyl-4-(1,2-dihydro-2-oxo-4-benzyloxymethyl-1-pyridinyl)-2H-benzo[b]pyran, 175. 6-cyano-2,2-dimethyl-4-(1,2-dihydro-2-oxo-5-benzyloxymethyl-1-pyridinyl)-2H-benzo[b]pyran, 176. 6-cyano-2,2-dimethyl-4-{1,2-dihydro-2-oxo-4-(1-benzyloxyethyl)-1-pyridinyl}-2H-benzo[b]pyran, 177. 6-cyano-2,2-dimethyl-4-{1,2-dihydro-2-oxo-4-(2-benzyloxyethyl)-1-pyridinyl}-2H-benzo[b]pyran, 178. 6-cyano-2,2-dimethyl-4-(1,2-dihydro-2-oxo-4,5-bis-benzyloxymethyl-1-pyridinyl)-2H-benzo[b]pyran, 179. 6-cyano-2,2-dimethyl-4-{1,2-dihydro-2-oxo-4-(1,4-dibenzyloxybutyl)-1-pyridinyl}-2H-benzo[b]pyran, 180. 6-cyano-2,2-dimethyl-4-(1,2-dihydro-2-oxo-3-methanesulfonyloxymethyl-1-pyridinyl)-2H-benzo[b]pyran, 181. 6-cyano-2,2-dimethyl-4-(1,2-dihydro-2-oxo-4-methanesulfonyloxymethyl-1-pyridinyl)-2H-benzo[b]pyran, 182. 6-cyano-2,2-dimethyl-4-(1,2-dihydro-2-2-oxo-5-methanesulfonyloxymethyl-1-pyridinyl)-2H-benzo[b]pyran, 183. 6-cyano-2,2-dimethyl-4-{1,2-dihydro-2-oxo-4-(1-methanesulfonyloxyethyl)-1-pyridinyl}-2H-benzo[b]pyran, 184. 6-cyano-2,2-dimethyl-4-{1,2-dihydro-2-oxo-4-(2-methanesulfonyloxyethyl)-1-pyridinyl}-2H-benzo[b]pyran, 185. 6-cyano-2,2-dimethyl-4-(1,2-dihydro-2-oxo-4,5-bis-methanesulfonyloxymethyl-1-pyridinyl)-2H-benzo[b]pyran, 186. 6-cyano-2,2-dimethyl-4-{1,2-dihydro-2-oxo-4-(1,4-dimethanesulfonyloxybutyl)-1-pyridinyl}-2H-benzo[b]pyran, 187. trans-3-hydroxy-6-trifluoromethyl-3,4-dihydro-2,2-dimethyl-4-(1,2-dihydro-2-oxo-4-t-butyldimethylsilyloxymethyl-1-pyridinyl)-2H-benzo[b]pyran, 188. 6-trifluoromethyl-2,2-dimethyl-4-(1,2-dihydro-2-oxo-4-t-butyldimethylsilyloxymethyl-1-pyridinyl)-2H-benzo[b]pyran, 189. 6-trifluoromethyl-2,2-dimethyl-4-(1,2-dihydro-2-oxo-4-hydroxymethyl-1-pyridinyl)-2H-benzo[b]pyran, 190. 6-cyano-2,2-dimethyl-4-(1,2-dihydro-2-oxo-4-vinyl-1-pyridinyl)-2H-benzo[b]pyran, 191. 6-cyano-2,2-dimethyl-4-(1,2-dihydro-2-oxo-4-formyl-1-pyridinyl)-2H-benzo[b]pyran, 192. 6-cyano-2,2-dimethyl-4-(1,2-dihydro-2-oxo-4-(3-hydroxypropyl)-1-pyridinyl}-2H-benzo[b]pyran, 193. 6-cyano-2,2-dimethyl-4-{1,2-dihydro-2-oxo-4-(4-hydroxybutyl)-1-pyridinyl}-2H-benzo[b]pyran.

In case that the compounds of this invention have asymmetric carbon atoms in the 3- and 4-positions of the chroman ring (sometimes in the substituent on the 1,2-dihydro-2-oxo-1-pyridinyl group), the compounds of the invention have a plurality of isomers. The objective compounds of this invention include not only the purely isolated optically active compounds, but also racemic mixtures thereof. Further, the compounds of this invention include the cis and trans isomers due to the conformations at the 3-and 4-positions, among which trans isomers are preferable.

Among the above-mentioned compounds, compound Nos. 2, 69, 72, 77, 81, 105 and 190 are preferable, and compound Nos. 69, 72, 77 and 105 are more preferable.

The synthetic route of the compounds of this invention are as shown below.

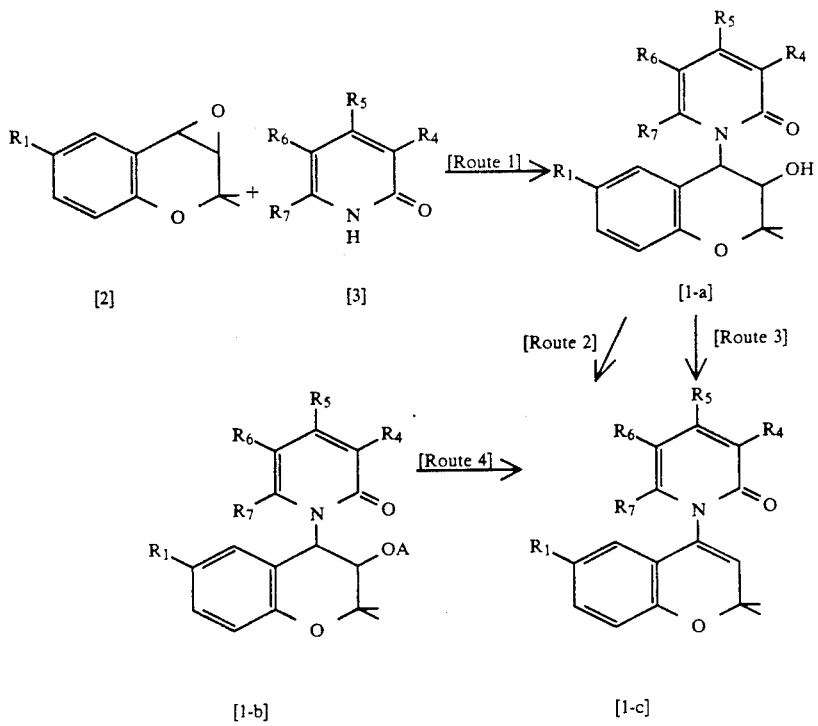

wherein $R_1$, $R_4$, $R_5$, $R_6$, $R_7$ and A are as defined above.

The compound [1] of this invention, wherein 1 inclusively means 1-a, 1-b and 1-c, can be produced by preparing [1-a] from a 6-substituted epoxy compound [2] and 1,2-dihydro-2-oxo-1-pyridine compound [3] via [Route 1], followed by preparing [1-b] from [1-a] via [Route 2] or by directly preparing [1-c] from [1-a] via [Route 3] or by preparing [1-c], via [Route 4], from the [1-b] obtained by [Route 2].

The processes for producing the compounds of this invention will be detailed below.

Route 1

The compound [1-a] of this invention is produced from a 6-substituted epoxy compound [2] and 1,2-dihydro-2-oxo-1-pyridine compound [3].

The concrete process for producing the compound [1-a] of this invention is as follows. Thus, the 1,2-dihydro-2-oxo-1-pyridine compound [3] is used in an amount of 0.5–10 moles, preferably about 1–3 moles, per mole of the 6-substituted epoxy compound [2]. If desired, a basic catalyst may be added, by which a better result can be obtained. As the basic catalyst, inorganic bases such as sodium hydride, lithium hydride, sodium hydroxide, potassium hydroxide and the like or organic bases such as pyridine, triethylamine, 4-dimethylaminopyridine and the like are used. The reaction is usually carried out in an organic solvent or in the absence of solvent, and preferably in an organic solvent. As the organic solvent, alcohols such as methanol, ethanol and the like, ethers such as tetrahydrofuran and the like or polar aprotic solvents such as dimethylformamide, dimethylsulfoxide and the like are used. The reaction temperature is not critical, and the reaction may be carried out with cooling, at ordinary temperature or with heating. Concretely speaking, the reaction is carried out at a temperature ranging from room temperature to the boiling point of the solvent for a period of 1–48 hours, whereby a good result is obtained. The compound [1-a] of this invention can be isolated by the conventional methods such as extraction, recrystallization, chromatography or the like.

When any one or two or more of $R_4$, $R_5$, $R_6$ and $R_7$ of compound [1-a] is (are) represented by formula $-Y-(OA)_n$ and A is hydrogen atom, it can be acylated by an acid anhydride such as acetic anhydride, propionic anhydride or the like or by an acid halide such as acetyl chloride, propionyl chloride or the like; and sulfonylated by an acid anhydride such as methanesulfonic anhydride, p-toluenesulfonic anhydride or the like or by a sulfonyl halide such as methanesulfonyl chloride, benzenesulfonyl chloride, p-toluenesulfonyl chloride or the like; and alkylated by an alkyl halide such as methyl iodide, ethyl bromide or the like or by an arylalkyl halide such as benzyl bromide, p-methoxybenzyl bromide or the like; and converted to a silyl derivative by a silyl halide such as t-butyldimethylsilyl chloride, t-butyldiphenylsilyl chloride, diethylisopropylsilyl chloride or the like; and nitrated by nitronium tetrafluoroborate, sulfuric acid-nitric acid, acetic acid-nitric acid or the like. When A is a lower alkylsulfonyl group having 1–6 carbon atoms or an arylsulfonyl group, it is nitrated by tetramethylammonium nitrate, tetraethylammonium nitrate, tetra-n-butylammonium nitrate or the like. These reagents are used in an amount of about 0.5–10 moles and preferably about 1–3 moles per mole of [1-a] ($-Y-(OA)_n$ group; hydroxyl compound or sulfonyl compound). If desired, a basic catalyst is added, whereby a better result can be obtained. As said basic catalyst, an inorganic base such as sodium hydride, lithium hydride, sodium hydroxide, potassium hydroxide or the like or an organic base such as pyridine, triethylamine, 4-dimethylaminopyridine or the like is used. The reaction is usually carried out in an organic solvent or in water or in the absence of solvent, and preferably in an organic solvent. As said organic solvent, aromatic hydrocarbons such as benzene, toluene, xylene and the like, alcohols such as methanol, ethanol and the like, ethers such as tetrahydrofuran and the like, halogenated hydrocarbons such as methylene chloride, chloroform and the like, and polar aprotic solvents such as dimethylformamide, dimethyl sulfoxide and the like are used. The reaction temperature is not critical, but the reaction may be carried out either with cooling or at ordinary temperature or with heating, for a period of 1–48hours. The compound [1-a] of this invention is isolated by the usual means such as extraction, recrystallization, chromatography or the like.

When any one or two or more of $R_4$, $R_5$, $R_6$ and $R_7$ in compound [1-a] is(are) represented by —CO—Z and Z is a hydroxyl group, it can be esterified by an alcohol such as methanol, ethanol, propanol, butanol or the like. If desired, an acid catalyst may be added, whereby a better result is obtained. As the acid catalyst, hydrochloric acid, sulfuric acid, thionyl chloride and the like can be used in an amount of about 0.01–100 moles, preferably 1–10 moles, per mole of [1-a] (—CO—Z group: hydroxyl compound). The reaction temperature is not critical, but the reaction can be carried out with cooling, at ordinary temperature or with heating for a period of 1–48 hours. The compound [1-a] can be isolated by usual means such as extraction, recrystallization, chromatography or the like. Examples of the compound [1-a] synthesizable via [Route 1] include Compounds 2, 123, 124, 125, 148 and the like.

Route 2

Concrete process for producing compound [1-b] of this invention will be detailed below.

In acylating, sulfonylating, alkylating or silylating the 3-hydroxyl group of chroman ring of compound [1-a], the reagents used for these reactions are acid anhydrides such as acetic anhydride, methanesulfonic anhydride and the like; acid halides such as acetyl chloride, methanesulfonyl chloride, p-toluenesulfonyl chloride and the like; lower alkyl halides such as methyl iodide, ethyl bromide and the like; arylalkyl halides such as benzyl bromide, p-methoxybenzyl bromide and the like, and silyl halides such as t-butyldimethylsilyl chloride, t-butyldiphenylsilyl chloride and the like.

In producing compound [1-b] by nitrating the 3-hydroxyl group of compound [1-a], the reagents used for this reaction are nitronium tetrafluoroborate, sulfuric acid-nitric acid, acetic acid-nitric acid and the like. When group A of compound [1-b] is a lower alkylsulfonyl group having 1–6 carbon atoms or an arylsulfonyl group, it is nitrated with tetramethylammonium nitrate, tetraethylammonium nitrate, tetra-n-butylammonium nitrate or the like to give a compound [1-b] wherein A is nitro.

These reagents are used in an amount of about 0.5–10 moles, preferably about 1–3 moles, per mole of compound [1-a]. If desired, a basic catalyst is added, whereby a better result can be obtained. As said basic catalyst, inorganic bases such as sodium hydride, lithium hydride, sodium hydroxide, potassium hydroxide and the like, or organic bases such as pyridine, triethylamine, 4-dimethylaminopyridine and the like are used. The reaction is usually carried out in an organic solvent or in water or in the absence of solvent, and preferably in an organic solvent. Examples of said organic solvent include alcohols such as methanol, ethanol and the like, ethers such as tetrahydrofuran and the like, halogenated hydrocarbons such as methylene chloride, chloroform and the like, and aprotic polar solvents such as dimethylformamide, dimethyl sulfoxide and the like. The reaction temperature is not critical, but the reaction can be carried out with cooling or at ordinary temperature or with heating for a period of 1–48 hours. The compound [1-b] of this invention can be isolated by usual means such as extraction, recrystallization, chromatography or the like.

When any one or two or more of $R_4$, $R_5$, $R_6$ and $R_7$ of compound [1-b] is(are) represented by —Y—(OA)$_n$ and A is hydrogen atom, lower alkylsulfonyl group having 1–6 carbon atoms or arylsulfonyl group or Z of —CO—Z is a hydroxyl group, various derivatives can be synthesized by the same methods as described in the paragraph of [Route 1]. Examples of the compound [1-b] synthesizable via [Route 2] include compounds 44, 117, 130, 154 and the like.

Route 3

Compound [1-c] can be synthesized via [Route 3] from compound [1-a] obtained by [Route 1].

The concrete process for producing compound [1-c] of this invention is as follows. Thus, it is produced by dehydrating compound [1-a]. The dehydrating reaction is carried out in the presence of an acid catalyst or a basic catalyst in an organic solvent. The organic solvents usable include alcohols such as methanol, ethanol and the like, ethers such as tetrahydrofuran and the like, halogenated hydrocarbons such as methylene chloride, chloroform and the like, and aprotic polar solvents such as dimethylformamide, dimethyl sulfoxide and the like. As the basic catalyst, inorganic bases such as sodium hydride, lithium hydride, sodium hydroxide, potassium hydroxide and the like, or organic bases such as pyridine, triethylamine, 4-dimethylaminopyridine and the like are used. As said acid catalyst, acids such as sulfuric acid, hydrochloric acid, hydrobromic acid and the like, or organic acids such as p-toluenesulfonic acid, camphorsulfonic acid and the like are used. These catalysts are used in an amount of about 0.1–10 moles, preferably about 0.5–2 moles, per mole of compound [1-a]. The reaction temperature is not critical, but the reaction may be carried out with cooling, at ordinary temperature or with heating. More concretely speaking, a better result can be obtained by carrying out the reaction at a temperature ranging from room temperature to the boiling point of the solvent for a period of 1–48 hours. The compound [1-c] of this invention can be isolated by usual means such as extraction, recrystallization, chromatography or the like. When any one or two or more of $R_4$, $R_5$, $R_6$ and $R_7$ of compound [1-c] is represented by —Y—(OA)$_n$ and A is hydrogen atom, lower alkylsulfonyl group having 1–6 carbon atoms or arylsulfonyl group or when Z of group —CO—Z is a hydroxyl group, various derivatives can be synthesized according to the same method as described in the paragraph of [Route 1].

Examples of the compound [1-c] synthesizable via [Route 3] include compounds 69, 70, 160, 167, 168, 181 and the like.

Route 4

Compound [1-c] of this invention can be synthesized via [Route 4] from the compound [1-b] obtained by [Route 2].

The concrete process for producing compound [1-c] of this invention is as follows. Thus, it can be synthesized by eliminating H and OA group from the compound [1-b]. The eliminating reaction is carried out in an organic solvent in the presence of an acid catalyst or a basic catalyst. The organic solvents used in this reaction include alcohols such as methanol, ethanol and the like, ethers such as tetrahydrofuran and the like, halogenated hydrocarbons such as methylene chloride, chloroform and the like, and aprotic polar solvents such as dimethylformamide, dimethyl sulfoxide and the like. As the basic catalyst, inorganic bases such as sodium hydride, lithium hydride, sodium hydroxide, potassium hydroxide and the like, or organic bases such as pyridine, triethylamine, 4-dimethylaminopyridine and the like are used. As said acid catalyst, acids such as sulfuric acid, hydrochloric acid, hydrobromic acid and the like or organic acids such as p-toluenesulfonic acid, camphorsulfonic acid and the like are used. These catalysts are used in an amount of about 0.01-10 moles, preferably 0.5-2 moles, per mole of compound [1-b]. The reaction temperature is not critical, but the reaction can be carried out with cooling or at ordinary temperature or with heating. More concretely speaking, a better result is obtained by carrying out the reaction at a temperature ranging from room temperature to the boiling point of the solvent for a period of 1-48 hours. The compound [1-c] of this invention thus formed can be isolated by usual means such as extraction, recrystallization, chromatography or the like.

When any one or two or more of $R_4$, $R_5$, $R_6$ and $R_7$ of compound [1-c] is(are) represented by —Y—(OA)$_n$— and A is hydrogen, lower alkylsulfonyl group having 1-6 carbon atoms or arylsulfonyl group or when Z of —CO—Z— is a hydroxyl group, various derivatives can be synthesized by the same methods as described in the paragraph of [Route 1]. Examples of the compound [1-c] synthesizable by [Route 4] include compounds 69, 70, 160, 167, 168, 169, 181 and the like.

Hereinunder, the production of compounds 69, 72, 77 and 105 which exhibited more desirable pharmaceutical activities will be described more concretely. The process for producing these compounds are shown in the following [Scheme 1].

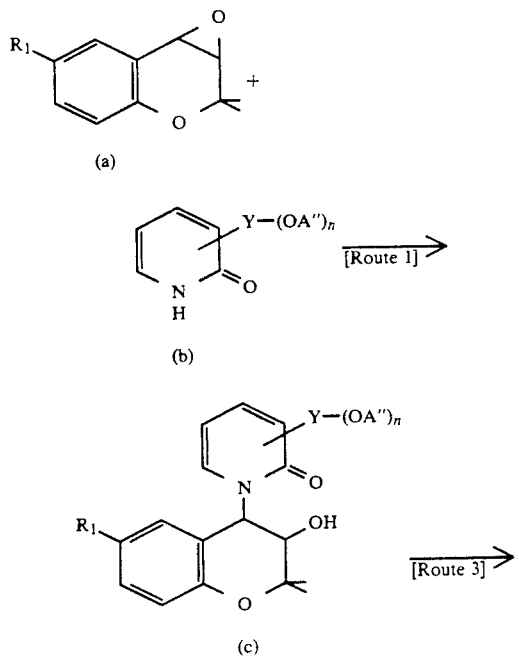

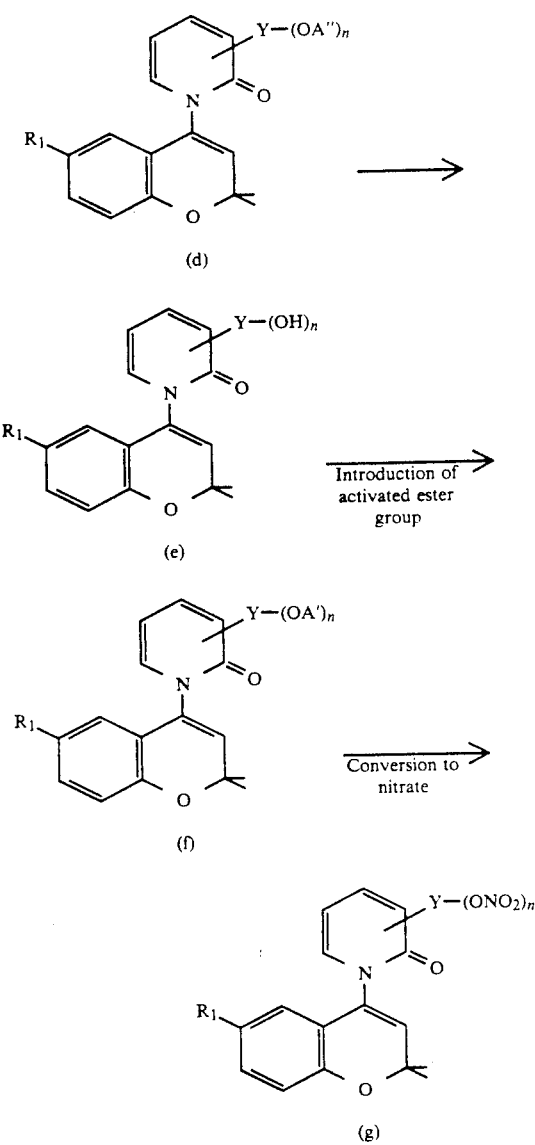

wherein $R_1$, Y and n are as defined above, A' is an activated ester group and A" is a hydrogen atom or a protective group.

In the reaction scheme presented above, examples of the activated ester group A' include sulfonic acid residues (residues formed by subtracting a hydroxyl group from a sulfonic acid group) such as tosyl group, methanesulfonyl group and the like. A protective group in A" includes a silyl type protective group, such as for example, t-butyldimethylsilyl group, t-butyldiphenylsilyl group, diethylisopropylsilyl group and the like.

Next, reaction scheme (1) will be explained.

Thus, one mole of 6-cyano- or 6-trifluoromethyl-2,2-dimethyl-3,4-epoxychroman (a) is reacted with about 0.5-10 moles, preferably about 1-3 moles, of a 1,2-dihydro-2-oxo-1H-pyridine derivative represented by general formula (b) in an organic solvent such as an alcohol (e.g. methanol, ethanol or the like) or an ether (e.g. tetrahydrofuran or the like) or an aprotic polar solvent (e.g. dimethylformamide, dimethyl sulfoxide or the like) or in the absence of solvent, in the presence of about 0.1-3 moles, preferably 0.3-2 moles, of a basic catalyst such as sodium hydride, lithium hydride, pyridine, triethylamine, 4-dimethylaminopyridine or the like and preferably in the presence of sodium hydride, pyridine or the like, at a temperature ranging from room temperature to the boiling point of the solvent, for a period of 1-100 hours, preferably 5-48 hours. As the after treatment, conventional methods can be adopted. Thus, the reaction mixture is concentrated under reduced pressure and the residue thus obtained is directly used in the subsequent reaction, or the residue is subjected to a column chromatography using silica gel or the like and eluted with an appropriate organic single solvent such as ethyl acetate, n-hexane or the like or their combination. In this way, the intended 2H-benzo[b]pyran derivative represented by general formula (c) can be obtained in a yield of 50-100%.

Examples of the 1,2-dihydro-2-oxo-1H-pyridine derivative represented by general formula (b) include 1,2-dihydro-2-oxo-4-t-butyldimethylsilyloxymethyl-1H-pyridine, 1,2-dihydro-2-oxo-4-(1-t-butyldimethylsilyloxyethyl)-1H-pyridine, 1,2-dihydro-2-oxo-4-(3-t-butyldimethylsilyloxypropyl)-1H-pyridine and the like. Examples of the 2H-benzo[b]pyran derivative represented by general formula (c) include trans-3-hydroxy-6-cyano or 6-trifluoromethyl-3,4-dihydro-2,2-dimethyl-4-(1,2-dihydro-2-oxo-4-t-butyldimethylsilyloxymethyl-1-pyridinyl)-2H-benzo[b]pyran, trans-3-hydroxy-6-cyano- or 6-trifluoromethyl-3,4-dihydro-2,2-dimethyl-4-{1,2-dihydro-2-oxo-4-(1-t-butyldimethylsilyloxethyl)-1-pyridinyl}-2H-benzo[b]pyran, trans-3-hydroxy-6-cyano- or 6-trifluoromethyl-3,4-dihydro-2,2-dimethyl-4-{1,2-dihydro-2-oxo-4-(3-t-butyldimethylsilyloxypropyl)-1-pyridinyl}-2H-benzo[b]pyran, and the like.

Then, the 2H-benzo[b]pyran derivative represented by general formula (c) is dehydrated according to the method of [Route 3], whereby a compound represented by general formula (d) is obtained Thus, a compound represented by general formula (c) is reacted in an alcohol such as methanol, ethanol or the like or in an ether such as tetrahydrofuran or the like or in a halogenated hydrocarbon such as methylene chloride, chloroform or the like or in an aprotic polar solvent such as dimethylformamide, dimethyl sulfoxide or the like and preferably in tetrahydrofuran, ethanol or dimethylformamide, in the presence of an inorganic basic catalyst such as sodium hydride, lithium hydride, potassium hydroxide or the like or an organic basic catalyst such as pyridine, triethylamine, 4-dimethylaminopyridine or the like or in the presence of an acid catalyst such as sulfuric acid, hydrochloric acid, hydrobromic acid, p-toluenesulfonic acid, camphorsulfonic acid or the like, at a temperature ranging from room temperature to the boiling point of the solvent, for a period of 1-48 hours and preferably 1-24 hours, provided that said catalyst is preferably used in an amount of 0.5-2 moles per mole of the compound (c).

As the method of after treatment, conventional methods can be adopted. Thus, after the reaction, water is added to the reaction mixture and then it is extracted with a hydrophobic organic solvent such as ether, ethyl acetate, toluene, chloroform or the like. The organic layer is successively washed with water and saturated aqueous solution of sodium chloride, dried over a drying agent such as anhydrous magnesium sulfate, anhydrous sodium sulfate or the like and then concentrated under reduced pressure. The residue thus obtained is directly used in the subsequent reaction, or it is purified by a column chromatography using silica gel, alumina or the like. Thus, a 2H-benzo[b]pyran derivative of which 3,4-positions have been dehydrated, represented by general formula (d), is obtained in a yield of 50-100%. Examples of the derivative represented by general formula (d) include 6-cyano- or 6-trifluoromethyl-2,2-dimethyl-4-(1,2-dihydro-2-oxo-4-t-butyldimethylsilyloxymethyl-1-pyridinyl)-2H-benzo[b]pyran, 6-cyano- or 6-trifluoromethyl-2,2-dimethyl-4-{1,2-dihydro-2-oxo-4-(1-t-butyldimethylsilyloxyethyl)-1-pyridinyl}-2H-benzo[b]pyran, 6-cyano- or 6-trifluoromethyl-2,2-dimethyl-4-{1,2-dihydro-2-oxo-4-(3-t-butyldimethylsilyloxypropyl)-1-pyridinyl}-2H-benzo[b]pyran, and the like.

Then, in the case where A" is a protecting group, the protecting group is removed from the compound of general formula (d) obtained by the method of [Route 3], whereby a compound of general formula (e) is obtained. Thus, the compound of general formula (d) is dissolved in an alcohol such as methanol, ethanol, or the like or a halogenated hydrocarbon such as methylene chloride, chloroform or the like. Then, about 0.2-10 moles, preferably about 1-5 moles, of a deprotecting reagent such as hydrochloric acid, sulfuric acid, p-toluenesulfonic acid, acetic acid, tetrabutylammonium fluoride or the like is added at a temperature ranging from $-30°$ C. to the boiling point of the solvent, preferably at $-10°$ C. to $30°$ C., and the resulting mixture is reacted at a temperature of $-10°$ C. to $30°$ C. for a period of 0.5-48 hours, preferably 1-24 hours.

As the after treatment, conventional methods can be adopted. Thus, the reaction mixture is concentrated under reduced pressure, and the residue is dissolved in water and extracted with a hydrophobic organic solvent such as ethyl acetate, methylene chloride, chloroform or the like. After extraction, the organic layer is separated and washed successively with saturated aqueous solution of sodium chloride and water and dried over anhydrous magnesium sulfate, anhydrous sodium sulfate or the like. After dryness, the organic solution is concentrated under reduced pressure, and the residue thus obtained is directly used in the subsequent reaction, or purified by a column chromatography using silica gel, alumina or the like to obtain the intended hydroxy derivative represented by general formula (e) in a yield of 50-100%.

The compound of general formula (e) thus obtained is converted to a compound represented by general formula (f) by introducing an eliminable group into the hydroxyl group of the compound (e). For example, one mole of the compound represented by general formula (e) is sulfonylated with about 0.5-10 moles, preferably about 1-5 moles, of an acid anhydride such as p-toluenesulfonic anhydride or the like or an acid halide such as methanesulfonyl chloride, p-toluenesulfonyl chloride or the like. As the solvent for this reaction, halogenated hydrocarbons such as methylene chloride, chloroform and the like, ethers such as tetrahydrofuran and the like, or aromatic hydrocarbons such as benzene, toluene and the like are used. The reaction is carried out in such an organic solvent in the presence of about 0.1-10 moles, preferably about 1-5 moles, of an inorganic base such as sodium hydride, lithium hydride or the like or an organic catalyst such as pyridine, triethylamine, 4-dimethylaminopyridine or the like, at a temperature ranging from $-30°$ C. to the boiling point of the solvent and preferably at $-10°$ C. to $50°$ C., for a period of 1-48 hours and preferably 1-24 hours.

The after treatment is as follows. Thus, after the reaction, the reaction mixture is diluted with water to stop the reaction, and then it is extracted with a hydrophobic organic solvent such as methylene chloride, chloroform or the like. The organic layer is successively washed with 0.1-6N aqueous solution of hydrochloric acid or sulfuric acid, water and saturated aqueous solution of sodium chloride and dried over a drier such as anhydrous magnesium sulfate or anhydrous sodium sulfate, after which the organic solvent is distilled off under reduced pressure. The residue is directly used for the subsequent reaction, or purified by a column chromatography using silica gel, alumina or the like. Thus, a sulfonyloxy derivative represented by general formula (f) is obtained in a yield of 50-100%.

Examples of the sulfonyloxy derivative represented by general formula (f) include 6-cyano- or 6-trifluoromethyl-2,2-dimethyl-4-(1,2-dihydro-2-oxo-4-methanesulfonyloxymethyl-1-pyridinyl)-2H-benzo[b]pyran, 6-cyano- or 6-trifluoromethyl-2,2-dimethyl-4-{1,2-dihydro-2-oxo-4-(1-methanesulfonyloxyethyl)-1-pyridinyl}-2H-benzo[b]pyran, 6-cyano- or 6-trifluoromethyl-2,2-dimethyl-4-{1,2-dihydro-2-oxo-4-(3-methanesulfonyloxypropyl)-1-pyridinyl}-2H-benzo[b]pyran, and the like.

Finally, the sulfonyloxy derivative represented by general formula (f) obtained above is converted to a nitrate to obtain the intended nitroxy derivative represented by general formula (g). Thus, one mole of a sulfonyloxy derivative represented by general formula (f) is mixed with about 1-10 moles and preferably about 1-5 moles, as expressed in terms of nitrate ion, of a nitrate forming agent in an inert solvent such as an aromatic hydrocarbon (e.g. benzene, toluene and the like) or a halogenated hydrocarbon (e.g. methylene chloride, chloroform and the like) at a temperature ranging from −30° C. to the boiling point of the solvent, preferably at −10° C. to 100° C., and the resulting mixture is reacted at a temperature ranging from room temperature (15° C.) to the boiling point of the solvent for a period of 0.25-48 hours, preferably 0.5-24 hours.

As examples of said nitrate-forming agent, mixtures of nitric acid and other acid such as mixed acid (nitric acid-sulfuric acid mixture), nitric acid-acetic acid mixture, nitric acid-sulfonic acid mixture and the like, tetrabenzylammonium nitrate, and tetraalkylammonium nitrate reagents such as tetramethylammonium nitrate, tetraethylammonium nitrate, tetra-n-butylammonium nitrate and the like can be referred to, among which tetra-n-butylammonium nitrate is preferable.

The after treatment is as follows. Thus, after the reaction, the reaction mixture is diluted with ice water, and extracted with a hydrophobic organic solvent such as ethyl acetate or the like. The organic layer is successively washed with water and saturated aqueous solution of sodium chloride and dried over a drier such as anhydrous magnesium sulfate, anhydrous sodium sulfate or the like, after which the solvent is evaporated under reduced pressure. The residue thus obtained is purified by a column chromatography using silica gel, alumina or the like to obtain the intended nitric ester represented by general formula (g) in a yield of 50-100%.

Examples of the nitro compound represented by general formula (g) include 6-cyano- or 6-trifluoromethyl-2,2-dimethyl-4-(1,2-dihydro-2-oxo-4-nitroxymethyl-1-pyridinyl)-2H-benzo[b]pyran, 6-cyano- or 6-trifluoromethyl-2,2-dimethyl-4-{1,2-dihydro-2-oxo-4-(1-nitroxyethyl)-1-pyridinyl}-2H-benzo[b]pyran, 6-cyano- or 6-trifluoromethyl-2,2-dimethyl-4-{1,2-dihydro-2-oxo-4-(3-nitroxypropyl)-1-pyridinyl}-2H-benzo[b]pyran, and the like.

The chroman derivatives represented by the following general formula (e′)

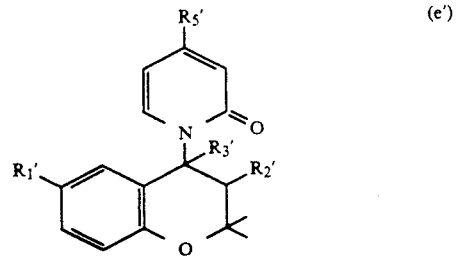

wherein $R_1'$ represents cyano group or halogenomethyl group, $R_2'$ forms a bond jointly with $R_3'$ or $R_2'$ represents hydroxy group or acetoxy group and $R_3'$ represents hydrogen atom, and $R_5'$ represents a lower alkyl group bonded with hydroxy group, is useful as an intermediate for a nitrated preferable compound. As particularly preferable substituents, there include cyano group or trifluoromethyl group as $R_1'$, $R_2'$ jointly with $R_3'$ forming a bond, hydroxymethyl group, hydroxyethyl group or hydroxypropyl group as $R_5'$.

Examples of the nitro compound represented by general formula (e′) include 6-cyano- or 6-trifluoromethyl-2,2-dimethyl-4-(1,2-dihydro-2-oxo-4-hydroxymethyl-1-pyridinyl)-2H-benzo[b]pyran, 6-cyano- or 6-trifluoromethyl-2,2-dimethyl-4-{1,2-dihydro-2-oxo-4-(1-hydroxyethyl)-1-pyridinyl}-2H-benzo[b]pyran, 6-cyano- or 6-trifluoromethyl-2,2-dimethyl-4-{1,2-dihydro-2-oxo-4-(3-hydroxypropyl)-1-pyridinyl}-2H-benzo[b]pyran, and the like.

When the compound of this invention is used as a medical drug, it is usually mixed with pharmaceutically acceptable additives such as carrier, excipient, diluent, solubilizer and the like and formed into preparations such as tablet including sugar-coated tablet and film-coated tablet, capsule, powder, granule, injection, drop, suppository, cataplasma and the like, after which it can be administered to mammals orally or non-orally with safety. In the preparations, the proportion of the compound of this invention is 0.01-99%, and the proportion of additives is 1-99.9%. Although the dose is dependent on the method of administration, it is usually about 0.01-20 mg/kg/day.

Next, the actions of the compound of this invention will be explained below.

1. Spasmolytic effect in isolated rat aorta and dog coronary artery

1) Rat aorta
  Method

The thoracic aorta of male SD rat was isolated and cut into 3 mm wide ring preparations. Each preparation was mounted in a 10 ml organ bath filled with Krebs-Henseleit solution by applying a resting tension of 1.0 g. The nutrient solution was maintained at 37° C. and aerated with a 95% $O_2$/5% $CO_2$ gas. The isometric tension of the preparation was measured with a FD pickup and recorded on a recorder.

After about one hour of equilibration time, a compound of this invention was cumulatively administered to the preparation contracted with 20 mM KCl, and its spasmolytic effect was examined. The spasmolytic action of the compound of this invention was expressed as percentage of inhibition, taking the maximal inhibition obtained with papavarine hydrochloride ($10^{-4}$M) as 100. The IC$_{50}$ value (50% inhibition) for the compound of this invention was determined from the concentration-response curve fitted by non-linear regressions with a personal computer, and its potency expressed in terms of $-\log$ IC$_{50}$ was shown as [mean value±standard error].

Results

| Compound | 20 mM KCl |
|---|---|
| Compound of Example 3 (Compound No. 2) | 7.29 ± 0.07 (n = 3) |
| Compound of Example 7 (Compound No. 44) | 5.18 ± 0.13 (n = 3) |
| Compound of Example 9 (Compound No. 161) | 6.28 ± 0.05 (n = 3) |
| Compound of Example 11 (Compound No. 69) | 8.48 ± 0.07 (n = 3) |
| Compound of Example 14 (Compound No. 162) | 6.86 ± 0.18 (n = 3) |
| Compound of Example 15 (Compound No. 70) | 6.87 ± 0.04 (n = 3) |
| Compound of Example 18 (Compound No. 160) | 6.09 ± 0.19 (n = 3) |
| Compound of Examples 24, 27 (Compound No. 190) | 7.22 ± 0.46 (n = 3) |
| Compound of Example 25 (Compound No. 191) | 6.35 ± 0.07 (n = 3) |
| Compound of Example 30 (Compound No. 72) | 7.17 ± 0.16 (n = 3) |
| Compound of Examples 34, 41 (Compound No. 192) | 5.95 ± 0.24 (n = 3) |
| Compound of Example 36 (Compound No. 77) | 7.90 ± 0.21 (n = 3) |
| Compound of Example 43 (Compound No. 91) | 6.99 ± 0.18 (n = 3) |
| Compound of Example 47 (Compound No. 193) | 5.87 ± 0.09 (n = 3) |
| Compound of Example 49 (Compound No. 81) | 7.40 ± 0.16 (n = 3) |
| Compound of Example 53 (Compound No. 105) | 8.23 ± 0.03 (n = 3) |

Discussions

This experiment revealed that the compounds of this invention exhibited an explicit spasmolytic effect on rat aorta. Theis $-\log$ IC$_{50}$ values were 5.18 to 8.48.

2) Dog coronary artery

Method

Ring preparations of coronary artery from mongrel dogs of either sex were prepared and isometric tension of the preparation was measured by the same method as above, except that the resting tension was adjusted to 1.5 g. For estimating the mechanism of action, the effect on the contraction caused by 80 mM KCl was also studied.

Results

| Compound | 20 mM KCl | 80 mM KCl |
|---|---|---|
| Compound of Example 11 (Compound No. 69) | 8.06 ± 0.22 (n = 3) | 4.90 ± 0.77 (n = 3) |
| Compound of Example 36 (Compound No. 77) | 8.67 ± 0.41 (n = 3) | 6.42 ± 0.20 (n = 3) |
| Compound of Example 49 (Compound No. 81) | 10.50 ± 0.95 (n = 4) | 6.64 ± 0.41 (n = 3) |

Discussions

The compounds of this invention exhibited an excellent spasmolytic effect on dog coronary artery contracted with 20 mM kCl. Compound Nos. 69, 77 and 81 also exhibited a spasmolytic effect on a contraction caused by 80 mM KCl, though their potencies are lower than those against the contraction caused by 20 mM KCl. This result suggests that, since these compounds contain a nitrate structure, an action as a nitrate is also responsible for their spasmolytic effect, in addition to the responsibility of a K channel opening action.

It is apparent from the above results that the compounds of this invention have a potent vasodilator action, whatever mechanism is responsible for the action, so that they are expected to be useful as new antihypertensive agent, therapeutic agent for angina pectoris, cardiac insufficiency, myocardial infarction and arrhythmia, drug for myocardial protection and for circulatory system such as cerebral circulation improver and the like, antiasthmatic agent, therapeutic agents for disorders due to the contraction of smooth muscles in the uterus and urinary passage, for example, dysuria, and antiepileptic agent, etc.

2. Bronchodilator effect in isolated tracheal smooth muscle

1) Guinea-pig trachea

Method

Hartley male guinea-pigs (NISSEIKEN) were stunned by a blow to the head and their tracheas were removed. Each trachea was carefully made into 20 small pieces so as not to injure them, and five pieces of them were linked together with a yarn to prepare tracheal strip chain. The preparation was suspended in 15 ml of an organ bath filled with a modified Krebs-Henseleit solution containing indomethacin (b $5\times10^{-6}$M) by applying a tension of 0.5 g. The solution was maintained at 35° C. and aerated with a 95% O$_2$/5% CO$_2$ gas. After an equilibration time of one hour, the experiment was carried out. The results were isometrically recorded on a Multipen Recorder (R-64VL, mfd. by Rika Denki Kogyo) through a transducer (TD-112S, mfd. by Nihon Kohden) and an input box (JD-112S, mfd. by Nihon Kohden).

Each preparation was made to attain the maximal contraction with carbachol ($3\times10^{-6}$ and $10^{-5}$M) and washed. When it reached an equilibrium, it was exposed to L-cysteine as an aminopeptidase inhibitor ($3\times10^{-3}$M). After thirty minutes, a contractive reaction was made to take place with leukotriene D$_4$ ($3\times10^{-9}$M). When the contraction had reached a constant value, a test drug ($10^{-8}$ to $3\times10^{-5}$M) was cumulatively applied into the bath at a dose ratio of 3. Finally, the maximal relaxation of each preparation was confirmed with papaverine.

Results

The relaxations given by each test drug at various concentrations were converted to percentages of relaxation, taking the maximal relaxation obtained with papaverine as 100. The maximal relaxation (%) of each test drug and $-\log$ of ED$_{30}$ (M) which is the dose of each test drug giving a percentage of relaxation of 30% as determined by a linear regression method from percentages of relaxation at two different doses are shown below.

| | Relaxing action on the contraction caused by leukotriene D$_4$ |
|---|---|
| | Maximal |

-continued

| Compound | −log[EX₃₀(M)] | relaxation % |
|---|---|---|
| Compound of Example 11 (Compound No. 69) | 6.65 | 93.9 |

It is apparent from the table that Compound 69 exhibits a strong relaxant effect on the isolated guinea pig tracheal smooth muscle contracted by leukotriene $D_4$.

It is apparent from the above that the compounds of this invention have a strong bronchodilator activity. Accordingly, they are expected to be useful as a new type bronchodilator which is effective not only on mild and medium paroxysms but also serious paroxysms. Further, for the same reasons as above, they are expected to be useful as agents for relaxing the symptoms of asthma but also the symptoms of asthmatic bronchitis, acute bronchitis, chronic bronchitis, pulmonary emphysema, pulmonary silicosis, pneumoconiosis, pulmonary tuberculosis, etc.

3 Acute toxicity in mice

Acute toxicity of the test drug was evaluated in mice, following intravenous administration. The $LD_{50}$ of the test drug was determined using up and down method.

| | $LD_{50}$ (mg/kg, i.v.) |
|---|---|
| Compound of Example 11 (Compound No. 69) | 81.2 |

In conclusion, the compound of this invention powerfully relaxes the smooth muscles such as vascular smooth muscle, bronchial smooth muscle and the like. Accordingly, the compound of this invention is expected to be effectively usable as a relaxant of smooth muscles for prevention and treatment of various symptoms due to the contraction of smooth muscles and for prevention and treatment of the diseases of the circulatory system.

EXAMPLE 1 (COMPOUND NO. 124)

Production of trans-3-hydroxy-6-cyano-3,4-dihydro-2,2-dimethyl-4-(1,2-dihydro-2-oxo-4-t-butyldimethylsilyloxymethyl-1-pyridinyl-2H-benzo[b]pyran At room temperature, 30 ml of ethanol and 1.29 ml of pyridine are added to a mixture of 4.02 g of 3,4-epoxy-3,4-dihydro-6-cyano-2,2-dimethyl-2H-benzo[b]pyran and 7.18 g of 1,2-dihydro-2-oxo-4-t-butyldimethylsilyloxymethyl-1H-pyridine, and the resulting mixture is reacted under reflux for 12 hours. The reaction mixture is concentrated under reduced pressure and the residue is isolated and purified by silica gel column chromatography using ¼ mixture of ethyl acetate/n-hexane as a developing solvent. Thus, 5.48 g of trans-3-hydroxy-6-cyano-3,4-dihydro-2,2-dimethyl-4-(1,2-dihydro-2-oxo-4-t-butyldimethylsilyloxymethyl-1-pyridinyl)-2H-benzo[b]pyran and, as a by-product, 1.96 g of trans-3-hydroxy-6-cyano-3,4-dihydro-2,2-dimethyl-4-{4-t-butyldimethylsilyloxymethyl-2-pyridyl)oxy}-2H-benzo[b]pyran are obtained.

¹H-NMR (200 MHz, CDCl₃) δ:0.13(s, 6H), 0.95(s, 9H), 1.37(s, 3H), 1.55(s, 3H), 3.85(dd, 1H), 4.23(d, 1H), 4.59(d, 2H), 6.20(dd, 1H), 6.32(d, 1H), 6.69(d, 1H), 6.84(d, 1H), 6.98(d, 1H), 7.10(m, 1H), 7.50(dd, 1H)

EXAMPLE 2 (COMPOUND NO. 148)

Production of trans-3-hydroxy-6-cyano-3,4-dihydro-2,2-dimethyl-4-(1,2-dihydro-2-oxo-4-methanesulfonyloxymethyl-1-pyridinyl)-2H-benzo[b]pyran.

In 12.2 ml of methanol is dissolved 1.32 g of the trans-3-hydroxy-6-cyano-3,4-dihydro-2,2-dimethyl-4-(1,2-dihydro-2-oxo-4-t-butyldimethylsilyloxymethyl-1-pyridinyl)-2H-benzo[b]pyran obtained in Example 1. Then, 3.15 ml of 4N hydrochloric acid in dioxane is added to the solution obtained above at 0° C., and reacted at room temperature for 2 hours. The reaction mixture is concentrated under reduced pressure, the residue is mixed with ethyl acetate and water, and the product is extracted into the ethyl acetate layer. The organic layer is washed with saturated aqueous solution of sodium chloride and dried over anhydrous sodium sulfate. After filtering off the inorganic matter, the filtrate is concentrated under reduced pressure. The residue is suspended in methylene chloride and the resulting crystalline matter is collected by filtration to obtain 0.91 g of a colorless crystalline product. Then, 326 mg of the colorless crystal thus obtained is dissolved in 4 ml of pyridine, and then 4 ml of a solution of 192 mg of methanesulfonic acid anhydride in anhydrous methylene chloride is added dropwise thereto at 0° C., and the resulting mixture is reacted at that temperature for 6 hours. After stopping the reaction by adding water, the reaction mixture is extracted with methylene chloride. The organic layer is successively washed with 2N aqueous solution of hydrochloric acid, water and saturated aqueous solution of sodium chloride and dried over anhydrous sodium sulfate. Then, the inorganic matter is filtered off and the filtrate is concentrated under reduced pressure and the resulting residue is purified by silica gel column chromatography by using 1/20 mixture of methanol/methylene chloride as a developing solvent. Thus, 201 mg of trans-3-hydroxy-6-cyano-3,4-dihydro-2,2-dimethyl-4-(1,2-dihydro-2-oxo-4-methanesulfonyloxymethyl-1-pyridinyl)-2H-benzo[b]pyran is obtained.

¹H-NMR (200 MHz, CDCl₃) δ:1.36(s, 3H), 1.56(s, 3H), 1.66(m, 1H), 3.14(s, 3H), 3.85(d, 1H), 5.09(d, 2H), 6.28(dd, 1H), 6.31(d, 1H), 6.68(s, 1H), 6.94(d, 1H), 6.98(d, 1H), 7.08(m, 1H), 7.51(dd, 1H)

EXAMPLE 3 (COMPOUND NO. 2)

Production of trans-3-hydroxy-6-cyano-3,4-dihydro-2,2-dimethyl-4-(1,2-dihydro-2-oxo-4-nitroxymethyl-1-pyridinyl)-2H-benzo[b]pyran In 3 ml of anhydrous toluene, is dissolved 315 mg of the trans-3-hydroxy-6-cyano-3,4-dihydro-2,2-dimethyl-4-(1,2-dihydro-2-oxo-4-methanesulfonyloxymethyl-1-pyridinyl)-2H-benzo[b]pyran obtained in Example 2. Then, 711 mg of tetra-n-butylammonium nitrate is added to the solution at room temperature, and reacted at 90° C. for one hour. After stopping the reaction by adding ice water, the reaction mixture is extracted with ethyl acetate. The organic layer is successively washed with water and saturated aqueous solution of sodium chloride, and dried over anhydrous sodium sulfate. Then, the inorganic matter is filtered off and the filtrate is concentrated under reduced pressure. The residue thus obtained is purified by silica gel column chromatography using 1/40 mixture of methanol/methylene chloride as a developing solvent. The crystal thus obtained is recrystallized from ethanol to give 137 mg of trans-3-hydroxy-6-cyano-3,4-dihydro-2,2-dimethyl-4-

(1,2-dihydro-2-oxo-4-nitroxymethyl-1-pyridinyl)-2H-benzo[b]pyran.

IR (KBr) cm⁻¹.
2315, 1665, 1645, 1580, 1280.

EXAMPLE 4 (COMPOUND NO. 130)

Production of trans-3-acetoxy-6-cyano-3,4-dihydro-2,2-dimethyl-4-(1,2-dihydro-2-oxo-4-t-butyldimethylsilyloxymethyl-1-pyridinyl)-2H-benzo[b]pyran In 15 ml of anhydrous methylene chloride, is dissolved 1.32 g of trans-3-hydroxy-6-cyano-3,4-dihydro-2,2-dimethyl-4-(1,2-dihydro-2-oxo-4-t-butyldimethylsilyloxymethyl-1-pyridinyl)-2H-benzo[b]pyran obtained in Example 1. Then, 0.49 ml of pyridine and 73 mg of 4-dimethylaminopyridine are added. Then, 0.43 ml of acetic anhydride is dropped thereinto at 0° C. and reacted at room temperature for 30 minutes. After stopping the reaction by adding water to the reaction mixture, it is extracted with ether. The organic layer is successively washed with water and saturated aqueous solution of sodium chloride and dried over anhydrous sodium sulfate. The inorganic matter is filtered off and the filtrate is concentrated under reduced pressure. The residue is purified by silica gel column chromatography using ⅓ mixture of ethyl acetate/methylene chloride as a developing solvent to obtain 1.45 g of trans-3-acetoxy-6-cyano-3,4-dihydro-2,2-dimethyl-4-(1,2-dihydro-2-oxo-4-t-butyldimethylsilyloxymethyl-1-pyridinyl)-2H-benzo[b]pyran.

$^1$H-NMR (200 MHz, CDCl$_3$) δ:0.13(s, 6H), 0.95(s, 9H), 1.44(s, 3H), 1.46(s, 3H), 2.03(s, 3H), 4.57(d, 2H), 5.33(d, 1H), 6.09(dd, 1H), 6.57(d, 1H), 6.64(m, 1H), 6.85(d, 1H), 6.97(d, 1H), 7.09(m, 1H), 7.49(dd, 1H).

EXAMPLE 5 (COMPOUND NO. 117)

Production of trans-3-acetoxy-6-cyano-3,4-dihydro-2,2-dimethyl-4-(1,2-dihydro-2-oxo-4-hydroxymethyl-1-pyridinyl)-2H-benzo[b]pyran In 15.0 ml of methanol, is dissolved 1.45 g of trans-3-acetoxy-6-cyano-3,4-dihydro-2,2-dimethyl-4-(1,2-dihydro-2-oxo-4-t-butyldimethylsilyloxy-1-pyridinyl)-2H-benzo[b]pyran obtained in Example 4. Then, 3.00 ml of 4N hydrochloric acid in dioxane is added thereto at 0° C. and reacted at room temperature for 2 hours. The reaction mixture is concentrated under reduced pressure, the residue is mixed with water and ethyl acetate, and the product is extracted by ethyl acetate. The organic layer is washed with saturated aqueous solution of sodium chloride and dried over anhydrous sodium sulfate. Then, the inorganic matter is filtered off and the filtrate is concentrated under reduced pressure. The residue is purified by silica gel column chromatography using ethyl acetate as a developing solvent to obtain 1.06 g of trans-3-acetoxy-6-cyano-3,4-dihydro-2,2-dimethyl-4-(1,2-dihydro-2-oxo-4-hydroxymethyl-1-pyridinyl)-2H-benzo[b]pyran.

$^1$H-NMR (200 MHz, CDCl$_3$) δ:1.43(s, 3H), 1.46(s, 3H), 2.04(s, 3H), 2.65(t, 1H), 4.57(d, 2H), 5.32(d, 1H), 6.18(dd, 1H), 6.55(d, 1H), 6.66(m, 1H), 6.93(d, 1H), 6.98(d, 1H), 7.01(m, 1H), 7.49(dd, 1H)

EXAMPLE 6 (COMPOUND NO. 154)

Production of trans-3-acetoxy-6-cyano-3,4-dihydro-2,2-dimethyl-4-(1,2-dihydro-2-oxo-4-methanesulfonyloxymethyl-1-pyridinyl)-2H-benzo[b]pyran In 10 ml of anhydrous methylene chloride, is dissolved 1.06 g of trans-3-acetoxy-6-cyano-3,4-dihydro-2,2-dimethyl-4-(1,2-dihydro-2-oxo-4-hydroxymethyl-1-pyridinyl)-2H-benzo[b]pyran obtained in Example 5. Then, 0.70 ml of pyridine and 71 mg of 4-dimethylaminopyridine are added. Then, 5 ml of a solution of 0.75 g of methanesulfonic acid anhydride in anhydrous methylene chloride is dropped into the solution at 0° C. and reacted at room temperature for 30 minutes. After stopping the reaction by adding water, the reaction mixture is extracted with ethyl acetate. The organic layer is successively washed with 1N aqueous solution of hydrochloric acid, water and saturated aqueous solution of sodium chloride and dried over anhydrous sodium sulfate. After filtering off the inorganic matter, the filtrate is concentrated under reduced pressure to obtain 1.28 g of trans-3-acetoxy-6-cyano-3,4-dihydro-2,2-dimethyl-4-(1,2-dihydro-2-oxo-4-methanesulfonyloxymethyl-1-pyridinyl)-2H-benzo[b]pyran.

$^1$H-NMR (200 MHz, CDCl$_3$) δ:1.44(s, 3H), 1.47(s, 3H), 2.04(s, 3H), 3.11(s, 3H), 5.07(s, 2H), 5.30(d, 1H), 6.18(dd, 1H), 6.54(d, 1H), 6.63(m, 1H), 6.96(d, 1H), 6.99(d, 1H), 7.08(m, 1H), 7.52(dd, 1H)

EXAMPLE 7 (COMPOUND NO. 44)

Production of trans-3-acetoxy-6-cyano-3,4-dihydro-2,2-dimethyl-4-(1,2-dihydro-2-oxo-4-nitroxymethyl-1-pyridinyl)-2H-benzo[b]pyran.

In 15 ml of anhydrous toluene, is dissolved 1.28 g of trans-3-acetoxy-6-cyano-3,4-dihydro-2,2-dimethyl-4-(1,2-dihydro-2-oxo-4-methanesulfonyloxymethyl-1-pyridinyl)-2H-benzo[b]pyran obtained in Example 6. Then, 2.70 g of tetra-n-butylammonium nitrate is added to the solution at room temperature, and the resulting mixture is reacted at 90° C. for 2 hours. After stopping the reaction by adding ice water, the reaction mixture is extracted with ethyl acetate. The organic layer is successively washed with water and saturated aqueous solution of sodium chloride and dried over anhydrous sodium sulfate. Then, the inorganic matter is filtered off, and the filtrate is concentrated under reduced pressure. The residue is purified by silica gel column chromatography using 3/2 mixture of ethyl acetate/n-hexane as a developing solvent. Thus, 1.07 g of trans-3-acetoxy-6-cyano-3,4-dihydro-2,2-dimethyl-4-(1,2-dihydro-2-oxo-4-nitroxymethyl-1-pyridinyl)-2H-benzo[b]pyran is obtained.

$^1$H-NMR (200 MHz, CDCl$_3$) δ:1.43(s, 3H), 1.46(s, 3H), 2.03(s, 3H), 5.29(d, 2H), 5.32(m, 1H), 6.16(dd, 1H), 6.54(d, 1H), 6.61(m, 1H), 6.97(d, 1H), 6.99(d, 1H), 7.08(m, 1H), 7.52(dd, 1H).

IR (KBr) cm⁻¹. 2310, 1750, 1670, 1640, 1595, 1280.

EXAMPLE 8 (COMPOUND NO. 168)

Production of 6-cyano-2,2-dimethyl-4-(1,2-dihydro-2-oxo-4-t-butyldimethylsilyloxymethyl-1-pyridinyl)-2H-benzo[b]pyran In 50 ml of anhydrous tetrahydrofuran, is dissolved 1.32 g of trans-3-hydroxy-6-cyano-3,4-dihydro-2,2-dimethyl-4-(1,2-dihydro-2-oxo-4-t-butyldimethylsilyloxymethyl-1-pyridinyl)-2H-benzo[b]pyran obtained is Example 1. Then, 0.12 g of 60% oily sodium hydride is added to the solution at room temperature and reacted under reflux for 4 hours. After stopping the reaction by adding water, the reaction mixture is extracted with ether. The organic layer is successively washed with water and saturated aqueous solution of sodium chloride and dried over anhydrous sodium sulfate. Then, the inorganic matter is filtered off and the filtrate is concentrated under reduced pressure. The residue is purified by silica gel column chromatography using 1/7 mixture of ethyl acetate/methylene chloride as a developing solvent. Thus, 1.04 g of 6-cyano-2,2-dimethyl-4-(1,2-dihydro-2-oxo-4-t-butyldimethylsilyloxymethyl-1-pyridinyl)-2H-benzo[b]pyran is obtained.

$^1$H-NMR (200 MHz, CDCl$_3$) δ:0.15(s, 6H), 0.97(s, 9H), 1.56(s, 3H), 1.62(s, 3H), 4.62(d, 2H), 5.80(s, 1H), 6.22(dd, 1H), 6.65(d, 1H), 6.90(d, 1H), 6.96(dd, 1H), 7.09(d, 1H), 7.44(dd, 1H).

EXAMPLE 9 (COMPOUND NO. 161)

Production of 6-cyano-2,2-dimethyl-4-(1,2-dihydro-2-oxo-4-hydroxymethyl-1-pyridinyl)-2H-benzo[b]pyran In 10.5 ml of methanol, is dissolved 1.04 g of 6-cyano-2,2-dimethyl-4-(1,2-dihydro-2-oxo-4-t-butyldimethylsilyloxymethyl-1-pyridinyl)-2H-benzo[b]pyran obtained in Example 8. Then, 2.59 ml of a 4N hydrochloric acid in dioxane is added to the solution at 0° C., and the resulting mixture is reacted at room temperature for 2 hours. The reaction mixture is concentrated under reduced pressure, the residue is mixed with ethyl acetate and water and the product is extracted into the ethyl acetate. The organic layer is washed with saturated aqueou solution of sodium chloride and dried over anhydrous sodium sulfate. The inorganic matter is filtered off, and the filtrate is concentrated under reduced pressure. The residue is purified by silica gel column chromatography using 1/20 mixture of methanol/methylene chloride as a developing solvent to obtain 0.76 g of 6-cyano-2,2-dimethyl-4-(1,2-dihydro-2-oxo-4-hydroxymethyl-1-pyridinyl)-2H-benzo[b]pyran.

$^1$H-NMR (200 MHz, CDCl$_3$) 6 :1.56(s, 3H), 1.62(s, 3H), 4.34(t, 1H), 4.57(d, 2H), 5.81(s, 1H), 6.30(dd, 1H), 6.68(d, 1H), 6.91(d, 1H), 6.93(s, 1H), 7.13(d, 1H), 7.45(dd, 1H).

EXAMPLE 10 (COMPOUND NO. 181)

Production of 6-cyano-2,2-dimethyl-4-(1,2-dihydro-2-oxo-4-methanesulfonyloxymethyl-1-pyridinyl)-2H-benzo[b]pyran.

In 7 ml of pyridine, is dissolved 655 mg of 6-cyano-2,2-dimethyl-4-(1,2-dihydro-2-oxo-4-hydroxymethyl-1-pyridinyl)-2H-benzo[b]pyran obtained in Example 9. Then, 7 ml of a solution of 555 mg of methanesulfonic acid anhydride in anhydrous methylene chloride is dropwise added to the solution, and the resulting mixture is reacted at that temperature for one hour. After stopping the reaction by adding water, the reaction mixture is extracted with methylene chloride. The organic layer is successively washed with 2N hydrochloric acid, water and saturated aqueous solution of sodium chloride and dried over anhydrous sodium sulfate. The inorganic matter is filtered off, and the filtrate is concentrated under reduced pressure. The residue thus obtained is purified by silica gel column chromatography using 1/10 mixture of methanol/methylene chloride as a developing solvent to obtain 756 mg of 6-cyano-2,2-dimethyl-4-(1,2-dihydro-2-oxo-4-methanesulfonyloxymethyl-1-pyridinyl)-2H-benzo[b]pyran.

$^1$H-NMR (200 MHz, CDCl$_3$) 6 :1.57(s, 3H), 1.62(s, 3H), 3.15(s, 3H), 5.12(s, 2H), 5.81(s, 1H), 6.30(dd, 1H), 6.66(m, 1H), 6.91(d, 1H), 6.94(s, 1H), 7.20(d, 1H), 7.46(dd, 1H)

EXAMPLE 11 (COMPOUND NO. 69)

Production of 6-cyano-2,2-dimethyl-4-(1,2-dihydro-2-oxo-4-nitroxymethyl-1-pyridinyl)-2H-benzo[b]pyran.

In 7 ml of anhydrous toluene, is dissolved 0.78 g of 6-cyano-2,2-dimethyl-4-(1,2-dihydro-2-oxo-4-methanesulfonyloxymethyl-1-pyridinyl)-2H-benzo[b]pyran obtained in Example 10. Then, 1.84 g of tetra-n-butylammonium nitrate is added to the solution at room temperature and reacted at 90° C. for one hour. After stopping the reaction by adding ice water, the reaction mixture is extracted with ethyl acetate. The organic layer is successively washed with water and saturated aqueous solution of sodium chloride and dried over anhydrous sodium sulfate. The inorganic matter is filtered off, and the filtrate is concentrated under reduced pressure. The residue thus obtained is roughly purified by silica gel column chromatography using 1/7 mixture of ethyl acetate/n-hexane as a developing solvent, and then further purified by silica gel column chromatography using 1/50 mixture of methanol/methylene chloride as a developing solvent to obtain 0.29 g of 6-cyano-2,2-dimethyl-4-(1,2-dihydro-2-oxo-4-nitroxymethyl-1-pyridinyl)-2H-benzo[b]pyran (Compound No. 69) and, as a by-product, 0.20 g of 6-cyano-2,2-dimethyl-4-(1,2-dihydro-2-oxo-4-formyl-1-pyridinyl)-2H-benzo[b]pyran. Compound No. 69:

$^1$H-NMR (200 MHz, CDCl$_3$) 6 :1.57(s, 3H), 1.62(s, 3H), 5.33(s, 2H), 5.81(s, 1H), 6.26(dd, 1H), 6.66(m, 1H), 6.92(d, 1H), 6.93(s, 1H), 7.21(d, 1H), 7.46(dd, 1H). IR (KBr) cm$^{-1}$.

2320, 1670, 1640, 1600, 1280.

EXAMPLE 12 (COMPOUND NO. 125)

Production of trans-3-hydroxy-6-cyano-3,4-dihydro-2,2-dimethyl-4-(1,2-dihydro-2-oxo-5-t-butyldimethylsilyloxymethyl-1-pyridinyl)-2H-benzo[b]pyran At room temperature, 30 ml of ethanol and 1.29 ml of pyridine are added to a mixture of 4.02 g of 3,4-epoxy-3,4-dihydro-6-cyano-2,2-dimethyl-2H-benzo[b]pyran and 7.18 g of 1,2-dihydro-2-oxo-5-t-butyldimethylsilyloxymethyl-1H-pyridine. The resulting mixture is reacted under reflux for 12 hours. After concentrating the reaction mixture under reduced pressure, the residue is purified by silica gel column chromatography using 1/1 mixture of ethyl acetate/n-hexane as a developing solvent to obtain 5.98 g of trans-3-hydroxy-6-cyano-3,4-dihydro-2,2-dimethyl-4-(1,2-dihydro-2-oxo-5-t-butyldimethylsilyloxymethyl-1-pyridinyl)-2H-benzo[b]pyran and, as a by-product, 1.84 g of trans-3-hydroxy-6-cyano-3,4-dihydro-2,2-dimethyl-4-{(5-t-butyldimethylsilyloxymethyl-2-pyridyl)oxy}-2H-bnezo[b]pyran.

$^1$H-NMR (200 MHz, CDCl$_3$) δ:0.02(s, 6H), 0.79(s, 9H), 1.36(s, 3H), 1.55(s, 3H), 3.87(dd, 1H), 4.14(d, 1H), 4.41(s, 2H), 6.35(d, 1H), 6.70(d, 1H), 6.85(m, 1H), 7.00(d, 1H), 7.12(m, 1H), 7.35(m, 1H), 7.52(dd, 1H).

EXAMPLE 13 (COMPOUND NO. 169)

Production of 6-cyano-2,2-dimethyl-4-(1,2-dihydro-2-oxo-5-t-butyldimethylsilyloxymethyl-1-pyridinyl)-2H-benzo[b]pyran.

In 50 ml of anhydrous tetrahydrofuran, is dissolved 1.32 g of trans-3-hydroxy-6-cyano-3,4-dihydro-2,2-dimethyl-4-(1,2-dihydro-2-oxo-5-t-butyldimethylsilyloxymethyl-1-pyridinyl)-2H-benzo[b]pyran obtained in Example 12. Then, 0.12 g of 60% oily sodium hydride is added to the solution at room temperature, and reacted under reflux for 3 hours. The reaction mixture is concentrated under reduced pressure, and the residue is mixed with ethyl acetate and water and extracted with the ethyl acetate. The organic layer is successively washed with water and saturated aqueous solution of sodium chloride and dried over anhydrous sodium sulfate. The inorganic matter is filtered off, and the filtrate is concentrated under reduced pressure. The residue is purified by silica gel column chromatography using ⅓ mixture of ethyl acetate/methylene chloride as a developing solvent to obtain 1.16 g of 6-cyano-2,2-dimethyl-4-(1,2-dihydro-2-oxo-5-t-butyldimethyl-silyloxymethyl-1-pyridinyl)-2H-benzo[b]pyran.

$^1$H-NMR (200 MHz, CDCl$_3$) δ:0.12(s, 6H), 0.92(s, 9H), 1.56(s, 3H), 1.62(s, 3H), 4.51(d, 2H), 5.80(s, 1H), 6.66(d, 1H), 6.91(d, 1H), 6.96(d, 1H), 7.08(m, 1H), 7.43(dd, 1H), 7.45(dd, 1H).

EXAMPLE 14 (COMPOUND NO. 162)

Production of 6-cyano-2,2-dimethyl-4-(1,2-dihydro-2-oxo-5-hydroxymethyl-1-pyridinyl)-2H-benzo[b]pyran In 11.5 ml of methanol, is dissolved 1.16 g of 6-cyano-2,2-dimethyl-4-(1,2-dihydro-2-oxo-5-t-butyldimethyl-silyloxymethyl-1-pyridinyl)-2H-benzo[b]pyran obtained in Example 13. Then, 2.87 ml of 4N hydrochloric acid in dioxane is added to the solution at 0° C., and reacted at room temperature for 1.5 hours. After stopping the reaction by adding water, the reaction mixture is extracted with ethyl acetate. The organic layer is washed with saturated aqueous solution of sodium chloride and dried over anhydrous sodium sulfate. The inorganic matter is filtered off, and the filtrate is concentrated under reduced pressure. The residue thus obtained is purified by silica gel column chromatography using 1/20 mixture of methanol/methylene chloride as a developing solvent to obtain 0.80 g of 6-cyano-2,2-dimethyl-4-(1,2-dihydro-2-oxo-5-hydroxymethyl-1-pyridinyl)-2H-benzo[b]pyran.

$^1$H-NMR (200 MHz, CDCl$_3$) δ:1.56(s, 3H), 1.62(s, 3H), 4.45(s, 2H), 4.46(m, 1H), 5.82(s, 1H), 6.64(d, 1H), 6.91(d, 1H), 6.95(d, 1H), 7.19(d, 1H), 7.45(dd, 1H), 7.53(dd, 1H).

EXAMPLE 15 (COMPOUND NO. 70)

Production of 6-cyano-2,2-dimethyl-4-(1,2-dihydro-2-oxo-5-nitroxymethyl-1-pyridinyl)-2H-benzo[b]pyran.

In 10 ml of anhydrous methylene chloride, is suspended 581 mg of 6-cyano-2,2-dimethyl-4-(1,2-dihydro-2-oxo-5-hydroxymethyl-1-pyridinyl)-2H-benzo[b]pyran obtained in Example 14. Then, 270 mg of nitronium tetrafluoroborate is added at room temperature and reacted at that temperature for 30 minutes. After stopping the reaction by adding ice water, the reaction mixture is extracted with methylene chloride, and the organic layer is washed with saturated aqueous solution of sodium chloride and dried over anhydrous sodium sulfate. The inorganic matter is filtered off, and the filtrate is concentrated under reduced pressure. The residue thus obtained is purified by silica gel column chromatography using 1/25 mixture of ethyl acetate/ether as a developing solvent. Thus, 328 mg of 6-cyano-2,2-dimethyl-4-(1,2-dihydro-2-oxo-5-nitroxymethyl-1-pyridinyl)-2H-benzo[b]pyran is obtained.

$^1$H-NMR (200 MHz, CDCl$_3$) δ :1.58(s, 3H), 1.62(s, 3H), 5.22(s, 2H), 5.83(s, 1H), 6.69(d, 1H), 6.91(d, 1H), 6.93(d, 1H), 7.32(d, 1H), 7.47(dd, 1H), 7.51(dd, 1H)

IR (KBr) cm$^{-1}$. 2320, 1670, 1630, 1610, 1280.

EXAMPLE 16 (COMPOUND NO. 123)

Production of trans-3-hydroxy-6-cyano-3,4-dihydro-2,2-dimethyl-4-(1,2-dihydro-2-oxo-3-t-butyldimethyl-silyloxymethyl-1-pyridinyl)-2H-benzo[b]pyran.

At room temperature, 30 ml of ethanol and 1.29 ml of pyridine are added to a mixture of 4.02 g of 3,4-epoxy-3,4-dihydro-6-cyano-2,2-dimethyl-2H-benzo[b]pyran and 7.18 g of 1,2-dihydro-2-oxo-3-t-butyldimethyl-silyloxymethyl-1H-pyridine. The resulting mixture is reacted under reflux for 12 hours. The reaction mixture is concentrated under reduced pressure, and the residue is purified by silica gel column chromatography using ¼ mixture of ethyl acetate/n-hexane as a developing solvent to obtain 5.08 g of trans-3-hydroxy-6-cyano-3,4-dihydro-2,2-dimethyl-4-(1,2-dihydro-2-oxo-3-t-butyl-dimethylsilyloxymethyl-1-pyridinyl)-2H-benzo[b]pyran and, as a by-product, 2.10 g of trans-3-hydroxy-6-cyano-3,4-dihydro-2,2-dimethyl-4-{(3-t-butyldimethylsilylox-ymethyl-2-pyridyl)oxy}-2H-benzo[b]pyran.

$^1$H-NMR (200 MHz, CDCl$_3$), δ:0.15(s, 3H), 0.16(s, 3H), 0.98(s, 9H), 1.36(s, 3H), 1.55(s, 3H), 3.87(dd, 1H), 4.00(d, 1H), 4.68(s, 2H), 6.34(d, 1H), 6.39(d, 1H), 6.81(dd, 1H), 6.98(d, 1H), 7.08(m, 1H), 7.50(dd, 1H), 7.60(dd, 1H).

EXAMPLE 17

Production of 6-cyano-2,2-dimethyl-4-(1,2-dihydro-2-oxo-3-t-butyldimethylsilyloxymethyl-1-pyridinyl)-2H-benzo[b]pyran.

In 50 ml of anhydrous tetrahydrofuran, is dissolved 1.32 g of trans-3-hydroxy-6-cyano-3,4-dihydro-2,2-dimethyl-4-(1,2-dihydro-2-oxo-3-t-butyldimethyl-silyloxymethyl-1-pyridinyl)-2H-benzo[b]pyran obtained in Example 16. Then, 0.12 g of 60% oily sodium hydride is added to the solution at room temperature and reacted under reflux for 3 hours. After stopping the reaction by adding water, the reaction mixture is extracted with ethyl acetate. The organic layer is washed with saturated aqueous solution of sodium chloride and dried over anhydrous sodium sulfate. The inorganic matter is filtered off, and the filtrate is concentrated under reduced pressure. The residue thus obtained is purified by silica gel column chromatography using 1/25 mixture of methanol/methylene chloride as a developing solvent to obtain 0.61 g of 6-cyano-2,2-dimethyl-4-(1,2-dihydro-2-oxo-3-t-butyldimethylsilyloxymeth-yl-1-pyridinyl)-2H-benzo[b]pyran.

$^1$H-NMR (200 MHz, CDCl$_3$) δ:0.14(s, 3H), 0.15(s, 3H), 0.98(s, 9H), 1.57(s, 3H), 1.61(s, 3H), 4.68(d, 2H), 5.80(s, 1H), 6.37(t, 1H), 6.89(s, 1H), 6.92(d, 1H), 7.08(dd, 1H), 7.45(dd, 1H), 7.65(dd, 1H)

EXAMPLE 18 (COMPOUND NO. 160)

Production of 6-cyano-2,2-dimethyl-4-(1,2-dihydro-2-oxo-3-hydroxymethyl-1-pyridinyl)-2H-benzo[b]pyran In 9.00 ml of methanol, is dissolved 877 mg of 6-cyano-2,2-dimethyl-4-(1,2-dihydro-2-oxo-3-t-butyl-dimethylsilyloxymethyl-1-pyridinyl)-2H-benzz[b]pyran obtained in Example 17. Then, 2.20 ml of 4N hydrochloric acid in dioxane is added to the solution at 0° C. and reacted at room temperature for one hour. After stopping the reaction by adding water, the reaction mixture is extracted with ethyl acetate. The organic layer is washed with saturated aqueous solution of sodium chloride and dried over anhydrous sodium sulfate. The inorganic matter is filtered off, and the filtrate is concentrated under reduced pressure. The residue thus obtained is purified by silica gel column chromatography using 1/20 mixture of methanol/methylene chloride as a developing solvent and further by silica gel column chromatography using 1/1 mixture of ethyl acetate/n-hexane as a developing solvent. Thus, 472 mg of 6-cyano-2,2-dimethyl-4-(1,2-dihydro-2-oxo-3-hydroxymethyl-1-pyridinyl)-2H-benzo[b]pyran is obtained.

¹H-NMR (200 MHz, CDCl₃) δ:1.56(s, 3H), 1.63(s, 3H), 3.26(t, 1H), 4.53–4.73(m, 2H), 5.83(s, 1H), 6.34(t, 1H), 6.91(s, 1H), 6.94(d, 1H), 7.15(d, 1H), 7.45(d, 1H), 7.49(m, 1H).

EXAMPLE 19

Production of trans-3-hydroxy-6-cyano-3,4-dihydro-2,2-dimethyl-4-(4-ethoxycarbonyl-1,2-dihydro-2-oxo-1-pyridinyl)-2H-benzo[b]pyran.

At room temperature, 60 ml of ethanol and 2.59 ml of pyridine are added to a mixture of 8.05 g of 3,4-epoxy-3,4-dihydro-6-cyano-2,2-dimethyl-2H-benzo[b]pyran and 9.19 g of 1,2-dihydro-2-oxo-4-methoxycarbonyl-1H-pyridine. The resulting mixture is reacted under reflux for 12 hours. The reaction mixture is concentrated under reduced pressure, and the residue is purified by silica gel column chromatography using ½ mixture of ethyl acetate/n-hexane as a developing solvent to obtain 8.93 g of trans-3-hydroxy-6-cyano-3,4-dihydro-2,2-dimethyl-4-(4-ethoxycarbonyl-1,2-dihydro-2-oxo-1-pyridinyl)-2H-benzo[b]pyran and, as a by-product, 3.39 g of trans-3-hydroxy-6-cyano-3,4-dihydro-2,2-dimethyl-4-{(4-ethoxycarbonyl-2-pyridyl)oxy}-2H-benzo[b]pyran.

¹H-NMR (200 MHz, CDCl₃) δ:1.37(s, 3H), 1.40(t, 3H), 1.57(s, 3H), 1.75(m, 1H), 3.87(d, 1H), 4.39(q, 2H), 6.33(d, 1H), 6.76(dd, 1H), 6.97(d, 1H), 7.00(s, 1H), 7.04(m, 1H), 7.28(d, 1H), 7.51(dd, 1H)

EXAMPLE 20

Production of trans-3-methanesulfonyloxy-6-cyano-3,4-dihydro-2,2-dimethyl-4-(4-ethoxycarbonyl-1,2-dihydro-2-oxo-1-pyridinyl)-2H-benzo[b]pyran.

In 7 ml of anhydrous methylene chloride, is dissolved 368 mg of trans-3-hydroxy-6-cyano-3,4-dihydro-2,2-dimethyl-4-(4-ethoxycarbonyl-1,2-dihydro-2-oxo-1-pyridinyl)-2H-benzo[b]pyran obtained in Example 19. Then, 4 ml of a solution of 607 mg of triethylamine in anhydrous methylene chloride is added. Then, 4 ml of a solution of 687 mg of methanesulfonyl chloride in anhydrous methylene chloride is dropwise added at 0° C. and reacted at room temperature for 2 hours. After stopping the reaction by adding water, the reaction mixture is extracted with methylene chloride. The organic layer is washed successively with 2N aqueous solution of hydrochloric acid, saturated aqueous solution of sodium hydrogen carbonate and saturated aqueous solution of sodium chloride and dried over anhydrous sodium sulfate. The inorganic matter is filtered off, and the filtrate is concentrated under reduced pressure. Thus, 446 mg of trans-3-methanesulfonyloxymethyl-6-cyano-3,4-dihydro-2,2-dimethyl-4-(4-ethoxycarbonyl-1,2-dihydro-2-oxo-1-pyridinyl)-2H-benzo[b]pyran is obtained.

¹H-NMR (200 MHz, CDCl₃) δ:1.40(t, 3H), 1.43(s, 3H), 1.64(s, 3H), 2.92(s, 3H), 4.39(q, 2H), 4.96(d, 1H), 6.66(d, 1H), 6.74(dd, 1H), 6.96(d, 1H), 7.01(d, 1H), 7.08(m, 1H), 7.32(d, 1H), 7.53(dd, 1H)

EXAMPLE 21

Production of 6-cyano-2,2-dimethyl-4-(4-ethoxycarbonyl-1,2-dihydro-2-oxo-1-pyridinyl)-2H-benzo[b]pyran In 8 ml of anhydrous tetrahydrofuran, is dissolved 250 mg of trans-3-methanesulfonyloxy-6-cyano-3,4-dihydro-2,2-dimethyl-4-(4-ethoxycarbonyl-1,2-dihydro-2-oxo-1-pyridinyl)-2H-benzo[b]pyran obtained in Example 20. Then, 112 mg of potassium t-butoxide is added at room temperature, and the resulting mixture is reacted at that temperature for 40 minutes. The reaction mixture is concentrated under reduced pressure and the residue is dissolved in methylene chloride, washed with saturated aqueous solution of sodium chloride, and dried over anhydrous magnesium sulfate. The inorganic matter is filtered off, and the filtrate is concentrated under reduced pressure. The residue is purified by silica gel column chromatography using ½ mixture of ethyl acetate/n-hexane as a developing solvent. Thus, 109 mg of 6-cyano-2,2-dimethyl-4-(4-ethoxycarbonyl-1,2-dihydro-2-oxo-1-pyridinyl)-2H-benzo[b]pyran is obtained.

¹H-NMR (200 MHz, CDCl₃) δ :1.42(t, 3H), 1.57(s, 3H), 1.63(s, 3H), 4.42(q, 2H), 5.83(s, 1H), 6.78(dd, 1H), 6.90(d, 1H), 6.93(d, 1H), 7.22(dd, 1H), 7.31(d, 1H), 7.46(dd, 1H).

EXAMPLE 22 (COMPOUND NO. 161)

Production of 6-cyano-2,2-dimethyl-4-(1,2-dihydro-2-oxo-4-hydroxymethyl-1-pyridinyl)-2H-benzo[b]pyran In 4 ml of anhydrous tetrahydrofuran, is dissolved 350 mg of 6-cyano-2,2-dimethyl-4-(4-ethoxycarbonyl-1,2-dihydro-2-oxo-1-pyridinyl)-2H-benzo[b]pyran obtained in Example 21. Then, 0.50 ml of 2.0M solution of lithium borohydride in tetrahydrofuran is added to the solution at room temperature and reacted at room temperature for 1.5 hours. After stopping the reaction by adding 0.2M phosphate buffer, the insoluble matter is solubilized by adding 2N aqueous hydrochloric acid. Then, the reaction mixture is extracted with ethyl acetate. The organic layer is washed with saturated aqueous solution of sodium chloride and dried over anhydrous sodium sulfate. The inorganic matter is filtered off, and the filtrate is concentrated under reduced pressure. The residue thus obtained is purified by silica gel column chromatography using 1/20 mixture of methanol/methylene chloride as a developing solvent to obtain 163 mg of 6-cyano-2,2-dimethyl-4-(1,2-dihydro-2-oxo-4-hydroxymethyl-1-pyridinyl)-2H-benzo[b]pyran.

EXAMPLE 23 (COMPOUND NO. 127)

Production of trans-3-hydroxy-6-cyano-3,4-dihydro-2,2-dimethyl-4-(1,2-dihydro-2-oxo-4-(2-t-butyldimethylsilyloxyethyl)-1-pyridinyl}-2H-benzo[b]pyran.

At room temperature, 27 ml of ethanol and 1.17 ml of pyridine are added to a mixture of 3.62 g of 3,4-epoxy-3,4-dihydro-6-cyano-2,2-dimethyl-2H-benzo[b]pyran and 6.84 g of 1,2-dihydro-2-oxo-4-(2-t-butyldimethylsilyloxyethyl))-1H-pyridine. The resulting mixture is reacted under reflux for 9 hours. The reaction mixture is concentrated under reduced pressure, and the residue is purified by silica gel column chromatography using ½ mixture of ethyl acetate/methylene chloride as a developing solvent to obtain 4.22 g of trans-3-hydroxy-6-cyano-3,4-dihydro-2,2-dimethyl-4-{1,2-dihydro-2-oxo-4-(2-t-butyldimethylsilyloxyethyl)-1-pyridinyl}-2H-benzo[b]pyran and, as a by-product, trans-3-hydroxy-6-cyano-3,4-dihydro-2,2-dimethyl-4-{4-(2-t-butyldimethylsilyloxyethyl)-2-pyridyloxy}-2H-benzo[b]pyran.

¹H-NMR (200 MHz, CDCl₃) δ:0.04(s, 6H), 0.88(s, 9H), 1.36(s, 3H), 1.55(s, 3H), 2.69(t, 2H), 3.83(d, 1H), 3.85(t, 2H), 4.17(d, 1H), 6.22(dd, 1H), 6.31(d, 1H), 6.54(s, 1H), 6.79(d, 1H), 6.97(d, 1H), 7.09(m, 1H), 7.50(dd, 1H).

EXAMPLE 24 (COMPOUND NO. 190)

Production of 6-cyano-2,2-dimethyl-4-(1,2-dihydro-2-oxo-4-vinyl-1-pyridinyl)-2H-benzo[b]pyran In 105 ml of anhydrous tetrahydrofuran, is dissolved 3.18 g of trans-3-hydroxy-6-cyano-3,4-dihydro-2,2-dimethyl-4-{1,2-dihydro-2-oxo-4-(2-t-butyldimethyl-silyloxyethyl)-1-pyridinyl}-2H-benzo[b]pyran obtained in Example 23. Then, 0.28 g of 60% oily sodium hydride is added to the solution at room temperature and reacted under reflux for one hour. After stopping the reaction by adding water, the reaction mixture is extracted with ether. The organic layer is washed with saturated aqueous solution of sodium chloride and dried over anhydrous sodium sulfate. The inorganic matter is filtered off, and the filtrate is concentrated under reduced pressure. The residue thus obtained is purified by silica gel column chromatography using ¼ mixture of ethyl acetate/methylene chloride as a developing solvent to obtain 2.01 g of 6-cyano-2,2-dimethyl-4-(1,2-dihydro-2-oxo-4-vinyl-1-pyridinyl)-2H-benzo[b]pyran.

$^1$H-NMR (200 MHz, CDCl$_3$) δ: 1.57(s, 3H), 1.62(s, 3H), 5.61(d, 1H), 5.85(s, 1H), 5.96(d, 1H), 6.49(dd, 1H), 6.56(d, 1H), 6.62(dd, 1H), 6.92(d, 1H), 6.96(d, 1H), 7.19(d, 1H), 7.46(dd, 1H).

EXAMPLE 25 (COMPOUND NO. 191)

Production of 6-cyano-2,2-dimethyl-4-(1,2-dihydro-2-oxo-4-formyl-1-pyridinyl)-2H-benzo[b]pyran.

In 200 ml of anhydrous methylene chloride, is dissolved 3.84 ml of oxalyl chloride. After cooling the resulting solution to −50° C. to −60° C., 6.24 ml of dimethyl sulfoxide is dropped thereinto and stirred at that temperature for 5 minutes. Then, 200 ml of a solution containing 12.3 g of 6-cyano-2,2-dimethyl-4-(1,2-dihydro-2-oxo-4-hydroxymethyl-1-pyridinyl)-2H-benzo[b]pyran obtained in Example 9 (or Example 22) in anhydrous methylene chloride is added at that temperature over a period of 25 minutes and reacted at that temperature for 20 minutes. After adding 27.9 ml of triethylamine to the reaction mixture and stirred at that temperature for 10 minutes, the temperature is slowly elevated to room temperature. After stirring the mixture at room temperature for an additional one hour, the reaction is stopped by adding water, and the reaction mixture is extracted with methylene chloride. The organic layer is washed with saturated aqueous solution of sodium chloride and dried over anhydrous sodium sulfate. The inorganic matter is filtered off and the filtrate is concentrated under reduced pressure. The residue is purified by silica gel column chromatography using 1/30 mixture of methanol/methylene chloride as a developing solvent. Thus, 12.2 g of 6-cyano-2,2-dimethyl-4-(1,2-dihydro-2-oxo-4-formyl-1-pyridinyl)-2H-benzo[b]pyran is obtained.

$^1$H-NMR (200 MHz, CDCl$_3$) δ: 1.58(s, 3H), 1.63(s, 3H), 5.84(s, 1H), 6.70(dd, 1H), 6.92(d, 1H), 6.94(d, 1H), 7.12(d, 1H), 7.29(d, 1H), 7.47(dd, 1H), 9.97(s, 1H)

EXAMPLE 26

Production of 6-cyano-2,2-dimethyl-4-{1,2-dihydro-2-oxo-4-(1-hydroxy-2-trimethylsilyl)ethyl-1-pyridinyl}-2H-benzo[b]pyran In 15 ml of anhydrous tetrahydrofuran, is dissolved 919 mg of 6-cyano-2,2-dimethyl-4-(1,2-dihydro-2-oxo-4-formyl-1-pyridinyl)-2H-benzo[b]pyran obtained in Example 25. Then, 30.6 ml of 1.0M solution of trimethylsilylmethylmagnesium chloride in ether is added at 0° C. and reacted at room temperature for one hour. After stopping the reaction by adding a saturated aqueous solution of ammonium chloride, and reaction mixture is extracted with ethyl acetate, and the organic layer is washed with saturated aqueous solution of sodium chloride and dried over anhydrous magnesium sulfate. The inorganic matter is filtered off, and the filtrate is concentrated under reduced pressure. The residue thus obtained is purified by silica gel column chromatography using ⅓ mixture of ethyl acetate/methylene chloride as a developing solvent. Thus, 883 mg of 6-cyano-2,2-dimethyl-4-{1,2-dihydro-2-oxo-4-(1-hydroxy-2-dimethyltrimethylsilyl)ethyl-1-pyridinyl}-2H-benzo[b]obtained.

$^1$H-NMR (200 MHz, CDCl$_3$) δ: 0.09(d, 9H), 1.06–1.22(m, 2H), 1.56(s, 3H), 1.62(s, 3H), 2.17(d, 1H), 4.72(m, 1H), 5.78(d, 1H), 6.34(dt, 1H), 6.59(s, 1H), 6.89(d, 1H), 6.92(m, 1H), 7.13(d, 1H), 7.44(dd, 1H).

EXAMPLE 27 (COMPOUND NO. 190)

Production of 6-cyano-2,2-dimethyl-4-(1,2-dihydro-2-oxo-4-vinyl-1-pyridinyl)-2H-benzo[b]pyran.

In 22 ml of anhydrous tetrahydrofuran, is dissolved 875 mg of 6-cyano-2,2-dimethyl-4-{1,2-dihydro-2-oxo-4-(1-hydroxy-2-trimethylsilylethyl)-1-pyridinyl}-2H-benzo[b]pyran obtained in Example 26. Then, 89 mg of 60% oily sodium hydride is added to the solution at room temperature and reacted at room temperature for 4 hours. After stopping the reaction by adding 0.2 M phosphate buffer, the reaction mixture is extracted with ethyl acetate. The organic layer is washed successively with water and saturated aqueous solution of sodium chloride and dried over anhydrous magnesium sulfate. Then, the inorganic matter is filtered off and the filtrate is concentrated under reduced pressure. The residue thus obtained is purified by silica gel column chromatography using 1/10 mixture of ethyl acetate/methylene chloride as a developing solvent. Thus, 493 mg of 6-cyano-2,2-dimethyl-4-(1,2-dihydro-2-oxo-4-vinyl-1-pyridinyl)-2H-benzo[b]pyran is obtained.

EXAMPLE 28 (COMPOUND NO. 163)

Production of 6-cyano-2,2-dimethyl-4-{1,2-dihydro-2-oxo-4-(1-hydroxy)ethyl-1-pyridinyl}-2H-benzo[b]pyran In 4 ml of anhydrous tetrahydrofuran, is dissolved 355 mg of 6-cyano-2,2-dimethyl-4-(1,2-dihydro-2-oxo-4-formyl-1-pyridinyl)-2H-benzo[b]pyran obtained in Example 25. Then, 1.73 ml of 0.94 M solution of methylmagnesium bromide in tetrahydrofuran is added at 0° C. and reacted first at that temperature for 50 minutes and then at room temperature for 20 minutes. After stopping the reaction by adding a saturated aqueous solution of ammonium chloride, the reaction mixture is extracted with ethyl acetate, and the organic layer is washed with saturated aqueous solution of sodium chloride and dried over anhydrous sodium sulfate. The inorganic matter is filtered off, and the filtrate is concentrated under reduced pressure. The residue thus obtained is purified by silica gel column chromatography using 1/1 mixture of methylene chloride/ethyl acetate as a developing solvent. Thus, 281 mg of 6-cyano-2,2-dimethyl-4-{1,2-dihydro-2-oxo-4-(1-hydroxy)ethyl-1-pyridinyl}-2H-benzo[b]pyran is obtained.

$^1$H-NMR (200 MHz, CDCl$_3$) δ: 1.50(dd, 3H), 1.56(s, 3H), 1.62(s, 3H), 2.42(dd, 1H), 4.76(m, 1H), 5.80(s, 1H), 6.34(ddd, 1H), 6.64(d, 1H), 6.90(d, 1H), 6.94(d, 1H), 7.14(d, 1H), 7.45(dd, 1H).

EXAMPLE 29 (COMPOUND NO. 183)

Production of 6-cyano-2,2-dimethyl-4-{1,2-dihydro-2-oxo-4-(1-methanesulfonyloxy)ethyl-1-pyridinyl}-2H-benzo[b]pyran.

In 3 ml of pyridine, is dissolved 276 mg of 6-cyano-2,2-dimethyl-4-(1,2-dihydro-2-oxo-4-(1-hydroxy)ethyl-1-pyridinyl}-2H-benzo[b]pyran obtained in Example 28. Then, 3 ml of a solution containing 224 mg of methanesulfonic acid anhydride in anhydrous methylene chloride is added at 0° C., and reacted at that temperature for one hour. After stopping the reaction by adding water, the reaction mixture is extracted with methylene chloride. The organic layer is washed successively with 2N hydrochloric acid, water and saturated aqueous solution of sodium chloride and dried over anhydrous sodium sulfate. The inorganic matter is filtered off and the filtrate is concentrated under reduced pressure. The residue is purified by silica gel column chromatography using 1/30 mixture of methanol/methylene chloride as a developing solvent. Thus, 356 mg of 6-cyano-2,2-dimethyl-4-{1,2-dihydro-2-oxo-4-(1-methanesulfonyloxy)-ethyl-1-pyridinyl}-2H-benzo[b]pyran is obtained.

$^1$H-NMR (200 MHz, CDCl$_3$) δ:1.57(s, 3H), 1.61(s, 3H), 1.73(d, 3H), 3.08(d, 3H), 5.59(q, 1H), 5.80(d, 1H), 6.30(ddd, 1H), 6.64(d, 1H), 6.91(d, 1H), 6.96(d, 1H), 7.26(s, 1H), 7.46(dd, 1H).

EXAMPLE 30 (COMPOUND NO. 72)

Production of 6-cyano-2,2-dimethyl-4-{1,2-dihydro-2-oxo-4-(1-nitroxyethyl)-1-pyridinyl}-2H-benzo[b]pyran In 3.5 ml of anhydrous toluene, is dissolved 343 mg of 6-cyano-2,2-dimethyl-4-{1,2-dihydro-2-oxo-4-(1-methanesulfonyloxy)ethyl-1-pyridinyl}-2H-benzo[b]pyran obtained in Example 29. Then, 782 mg of tetra-n-butylammonium nitrate is added to the solution at room temperature and reacted at 90° C. for 3 hours. After stopping the reaction by adding ice water, the reaction mixture is extracted with ethyl acetate. The organic layer is washed successively with water and saturated aqueous solution of sodium chloride and dried over anhydrous sodium sulfate. The inorganic matter is filtered off, and the filtrate is concentrated under reduced pressure. The residue thus obtained is purified by silica gel column chromatography using 1/20 mixture of ethyl acetate/methylene chloride as a developing solvent. Thus, 252 mg of 6-cyano-2,2-dimethyl-4-{1,2-dihydro-2-oxo-4-(1-nitroxyethyl)-1-pyridinyl}-2H-benzo[b]pyran (Compound No. 72) is obtained.

$^1$H-NMR (200 MHz, CDCl$_3$) δ:1.56(s, 3H), 1.62(s, 3H), 1.66(dd, 3H), 5.76(q, 1H), 5.81(s, 1H), 6.26(ddd, 1H), 6.64(m, 1H), 6.91(d, 1H), 6.97(d, 1H), 7.20(dd, 1H), 7.46(dd, 1H). IR (KBr) cm$^{-1}$. 2310, 1670, 1630, 1590, 1275.

EXAMPLE 31

Production of 6-cyano-2,2-dimethyl-4-{1,2-dihydro-2-oxo-4-(1-hydroxy-2-ethoxycarbonylethyl)-1-pyridinyl}-2H-benzo[b]pyran In 40 ml of anhydrous tetrahydrofuran, is dissolved 3.64 ml of diisopropylamine. The resulting solution is cooled to 0° C. After dropping 15.4 ml of 1.62M solution of n-butyllithium in n-hexane thereto and stirring the resulting mixture for 10 minutes at that temperature, it is cooled to −78° C. and stirred for 20 minutes. Then, 2.34 ml of ethyl acetate is dropped and stirred at that temperature for 30 minutes. Then, 160 ml of an anhydrous tetrahydrofuran solution containing 6.13 g of the 6-cyano-2,2-dimethyl-4-(1,2-dihydro-2-oxo-4-formyl-1-pyridinyl)-2H-benzo[b]pyran obtained in Example 25 is added at that temperature over a period of 55 minutes, and the whole mixture is reacted first at that temperature for one hour, then at 0° C. for 30 minutes and then at room temperature for 30 minutes. After stopping the reaction by adding 0.2M phosphate buffer, the reaction mixture is extracted with ethyl acetate. The organic layer is washed successively with 2N aqueous hydrochloric acid, water and saturated aqueous solution of sodium chloride and dried over anhydrous sodium sulfate. The inorganic matter is filtered off, and the filtrate is concentrated under reduced pressure. The residue thus obtained is purified by silica gel column chromatography using 3/1 mixture of ethyl acetate/n-hexane as a developing solvent. Thus, 5.88 g of 6-cyano-2,2-dimethyl-4-{1,2-dihydro-2-oxo-4-(1-hydroxy-2- ethoxycarbonylethyl)- 1-pyridinyl}-2H-benzo[b]pyran is obtained.

$^1$H-NMR (200 MHz, CDCl$_3$) δ:1.31(t, 3H), 1.56(s, 3H), 1.62(s, 3H), 2.71–2.79(m, 2H), 3.68(m, 1H), 4.23(q, 2H), 5.00(dd, 1H), 5.80(s, 1H), 6.36(dd, 1H), 6.66(s, 1H), 6.90(d, 1H), 6.94(d, 1H), 7.15(d, 1H), 7.45(dd, 1H).

EXAMPLE 32

Production of 6-cyano-2,2-dimethyl-4-{1,2-dihydro-2-oxo-4-(1-phenoxythiocarbonyloxy-2-ethoxycarbonylethyl)-1-pyridinyl}-2H-benzo[b]pyran In 10 ml of acetonitrile, is dissolved 314 mg of 6-cyano-2,2-dimethyl-4-{2-oxo-4-(1-hydroxy-2-ethoxycarbonylethyl)-1-pyridinyl}-2H-benzo[b]pyran obtained in Example 31. Then, 195 mg of 4-dimethylaminopyridine and 0.17 ml of phenoxythiocarbonyl chloride are added at room temperature and reacted at that temperature for 19.5 hours. After stopping the reaction by adding 0.1M aqueous solution of sodium hydrogen carbonate, the reaction mixture is extracted with ethyl acetate. The organic layer is washed successively with water and saturated aqueous solution of sodium chloride and dried over anhydrous sodium sulfate. The inorganic matter is filtered off and the filtrate is concentrated under reduced pressure. The residue is purified by silica gel column chromatography using ⅔ mixture of ethyl acetate/n-hexane. Thus, there are obtained 77 mg of 6-cyano-2,2-dimethyl-4-{1,2-dihydro-2-oxo-4-(1-phenoxythiocarbonyloxy-2-ethoxycarbonylethyl)-1-pyridinyl}-2H-benzo[b]pyran and, as a by-product, 20 mg of 6-cyano-2,2-dimethyl-4-{1,2-dihydro-2-oxo-4-(2-ethoxycarbonylethenyl)-1-pyridinyl}-2H-benzo[b]pyran.

$^1$H-NMR (200 MHz, CDCl$_3$) δ:1.32(t, 3H), 1.56(s, 3H), 1.62(s, 3H), 3.05(ddd, 2H), 4.24(q, 2H), 5.82(s, 1H), 6.34(d, 1H), 6.46(m, 1H), 6.72(s, 1H), 6.91(d, 1H), 6.97(t, 1H), 7.10(s, 1H), 7.14(s, 1H), 7.19(dd, 1H), 7.32(d, 1H), 7.40(s, 1H), 7.43(s, 1H), 7.46(dd, 1H).

EXAMPLE 33

Production of 6-cyano-2,2-dimethyl-4-{1,2-dihydro-2-oxo-4-(2-ethoxycarbonylethyl)-1-pyridinyl}-2H-benzo[b]pyran In 3 ml of anhydrous toluene, is dissolved 73 mg of 6-cyano-2,2-dimethyl-4-{1,2-dihydro-2-oxo-4-(1-phenoxythiocarbonyloxy-2-ethoxycarbonylethyl)-1-pyridinyl}-2H-benzo[b]pyran obtained in Example 32. Then, 45 mg of 2,2'-azobisisobutyronitrile and 80 mg of tri-n-butyltin hydride are added to the solution at room temperature, and the resulting mixture is reacted at 100° C. for 30 minutes. After the reaction, the reaction mixture is directly purified by silica gel column chromatography to obtain 42 mg of 6-cyano-2,2-dimethyl-4-}-1,2-dihydro-2-oxo-4-(2-ethoxycarbonylethyl)-1pyridinyl}-2H-benzo[b]pyran.

$^1$H-NMR (200 MHz, CDCl$_3$) δ:1.29(t, 3H), 1.56(s, 3H), 1.61(s, 3H), 2.67(t, 2H), 2.86(t, 2H), 4.18(q, 2H), 5.78(s, 1H), 6.17(dd, 1H), 6.47(d, 1H), 6.90(d, 1H), 6.95(d, 1H), 7.07(d, 1H), 7.44(dd, 1H).

EXAMPLE 34

Production of 6-cyano-2,2-dimethyl-4-{1,2-dihydro-2-oxo-4-(3-hydroxypropyl)-1-pyridinyl}-2H-benzo[b]pyran In 16 ml of dioxane, is dissolved 617 mg of 6-cyano-2,2-dimethyl-4-{1,2-dihydro-2-oxo-4-(2-ethoxycarbonylethyl)-1-pyridinyl}-2H-benzo[b]pyran obtained in Example 33. Then, 16 ml of an aqueous solution containing 617 m of sodium borohydride is added at room temperature and reacted first at room temperature for 1.5 hours and then at 60° C. for one hour. After stopping the reaction by adding 20 ml of 2M aqueous hydrochloric acid, the reaction mixture is extracted with ethyl acetate. The organic layer is washed with saturated aqueous solution of sodium chloride and dried over anhydrous magnesium sulfate. The inorganic matter is filtered off and the filtrate is concentrated under reduced pressure. The residue is purified by silica gel column chromatography using 1/10 mixture of methanol/methylene chloride as a developing solvent. Thus, 493 mg of 6-cyano-2,2-dimethyl-4-(1,2-dihydro-2-oxo-4-(3-hydroxypropyl)-1-pyridinyl}-2H-benzo[b]pyran is obtained.

$^1$H-NMR (200 MHz, CDCl$_3$) δ:1.56(s, 3H), 1.62(s, 3H), 1.76(m, 1H), 1.83-1.99(m, 2H), 2.64(t, 2H), 3.73(t, 2H), 5.79(s, 1H), 6.18(dd, 1H), 6.49(s, 1H), 6.90(d, 1H), 6.96(d, 1H), 7.07(d, 1H), 7.44(dd, 1H).

EXAMPLE 35

Production of cyano-2,2-dimethyl-4-{1,2-dihydro-2-oxo-4-(3-methanesulfonyloxypropyl)-1-pyridinyl}-2H-benzo[b]pyran In 4 ml of pyridine, is dissolved 387 mg of 6-cyano-2,2-dimethyl-4-{1,2-dihydro-2-oxo-4-(3-hydroxypropyl)-1-pyridinyl}-2H-benzo[b]pyran obtained in Example 34 (or Example 41). Then, 4 ml of a solution of 301 mg of methanesulfonic acid anhydride in anhydrous methylene chloride is dropwise added to the solution obtained above at 0° C. and reacted at that temperature for 30 minutes. After stopping the reaction by adding water, the reaction mixture is extracted with methylene chloride. The organic layer is washed successively with 2N aqueous hydrochloric acid, water and saturated aqueous solution of sodium chloride and dried over anhydrous magnesium sulfate. The inorganic matter is filtered off and the filtrate is concentrated under reduced pressure. The residue is purified by silica gel column chromatography using 1/15 mixture of methanol/methylene chloride as a developing solvent to obtain 403 mg of 6-cyano-2,2-dimethyl-4-{1,2-dihydro-2-oxo-4-(3-methanesulfonyloxypropyl)-1-pyridinyl}-2H-benzo[b]pyran.

$^1$H-NMR (200 MHz, CDCl$_3$) δ:1.56(s, 3H), 1.62(s, 3H), 2.04-2.21(m, 2H), 2.68(t, 2H), 3.06(s, 3H), 4.32(t, 2H), 5.80(s, 1H), 6.16(dd, 1H), 6.48(d, 1H), 6.90(d, 1H), 6.95(d, 1H), 7.10(d, 1H), 7.45(dd, 1H).

EXAMPLE 36 (COMPOUND NO. 77)

Production of 6-cyano-2,2-dimethyl-4-{1,2-dihydro-2-oxo-4-(3-nitroxypropyl)-1-pyridinyl}-2H-benzo[b]pyran In 8 ml of anhydrous toluene, is dissolved 396 mg of 6-cyano-2,2-dimethyl-4-{1,2-dihydro-2-oxo-4-(3-methanesulfonyloxypropyl)-1-pyridinyl}-2H-benzo[b]pyran obtained in Example 35. Then, 873 mg of tetra-n-butylammonium nitrate is added to the solution at room temperature and reacted at 90° C. for 2 hours. After stopping the reaction by adding ice water, the reaction mixture is extracted with ethyl acetate. The organic layer is washed successively with water and saturated aqueous solution of sodium chloride and dried over anhydrous sodium sulfate. The inorganic matter is filtered off, and the filtrate is concentrated under reduced pressure. The residue thus obtained is purified by silica gel column chromatography using 1/10 mixture of ethyl acetate/methylene chloride as a developing solvent. Thus, 333 mg of 6-cyano-2,2-dimethyl-4-{1,2-dihydro-2-oxo-4-(3-nitroxypropyl)-1-pyridinyl}-2H-benzo[b]pyran (Compound No. 77) is obtained.

$^1$H-NMR (200 MHz, CDCl$_3$) δ:1.56(s, 3H), 1.62(s, 3H), 2.02-2.19(m, 2H), 2.66(t, 2H), 4.55(t, 2H), 5.80(s, 1H), 6.14(dd, 1H), 6.46(s, 1H), 6.90(d, 1H), 6.95(d, 1H), 7.10(d, 1H), 7.45(dd, 1H).

IR (KBr) cm$^{-1}$. 2310, 1670, 1630, 1595, 1280

EXAMPLE 37

Production of 6-cyano-2,2-dimethyl-4-{1,2-dihydro-2-oxo-4-(1,3-dihydroxypropyl)-1-pyridinyl}-2H-benzo[b]pyran In 50 ml of dioxane, is dissolved 3.87 g of 6-cyano-2,2-dimethyl-4-{1,2-dihydro-2-oxo-4-(1-hydroxy-2-ethoxycarbonylethyl)-1-pyridinyl}-2H-benzo[b]pyran obtained in Example 31. Then, 50 ml of an aqueous solution containing 3.71 g of sodium borohydride is added at room temperature and reacted at room temperature for one hour. After stopping the reaction by adding 100 ml of 2M aqueous hydrochloric acid, the reaction mixture is extracted with ethyl acetate. The organic layer is washed with saturated aqueous solution of sodium chloride and dried over anhydrous magnesium sulfate. The inorganic matter is filtered off and the filtrate is concentrated under reduced pressure. The residue is purified by silica gel column chromatography using 1/10 mixture of methanol/methylene chloride as a developing solvent. Thus, 2.32 g of 6-cyano-2,2-dimethyl-4-{1,2-dihydro-2-oxo-4-(1,3-dihydroxypropyl)-1-pyridinyl}-2H-benzo[b]pyran is obtained.

$^1$H-NMR (200 MHz, CDCl$_3$) δ:1.56(s, 3H), 1.62(s, 3H), 1.82-2.01(m, 2H), 3.24(m, 1H), 3.78-3.99(m, 2H), 4.49(m, 1H), 4.83(m, 1H), 5.82(s, 1H), 6.37(ddd, 1H), 6.69(d, 1H), 6.90(d, 1H), 6.92(d, 1H), 7.17(d, 1H), 7.45(dd, 1H).

EXAMPLE 38

Production of 6-cyano-2,2-dimethyl-4-{1,2-dihydro-2-oxo-4-(1-hydroxy-3-t-butyldimethylsilyloxypropyl)-1-pyridinyl}-2H-benzo[b]pyran.

In 15 ml of anhydrous methylene chloride, is dissolved 1.06 g of 6-cyano-2,2-dimethyl-4-{1,2-dihydro-2-oxo-4-(1,3-dihydroxypropyl)-1-pyridinyl}-2H-benzo[b]pyran obtained in Example 37. Thereto are added 0.46 ml of triethylamine and 6 ml of a solution containing 0.48 g t-butyldimethylsilyl chloride in anhydrous methylene chloride at 0° C., and the resulting mixture is reacted at room temperature for 8 hours. After stopping the reaction by adding 0.2M phosphate buffer, the reaction mixture is extracted with methylene chloride. The organic layer is washed with saturated aqueous solution of sodium chloride and dried over anhydrous sodium sulfate. The inorganic matter is filtered off and the filtrate is concentrated under reduced pressure. Thus, 1.46 g of 6-cyano-2,2-dimethyl-4-{1,2-dihydro-2-oxo-4-(1-hydroxy-3-t-butyldimethylsilyloxypropyl)-1-pyridinyl}-2H-benzo[b]pyran is obtained.

$^1$H-NMR (200 MHz, CDCl$_3$) δ:0.13(s, 6H), 0.94(s, 9H), 1.56(s, 3H), 1.62(s, 3H), 1.89–2.05(m, 2H), 3.95(dt, 2H), 4.19(dd, 1H), 4.84(m, 1H), 5.80(s, 1H), 6.36(ddd, 1H), 6.65(d, 1H), 6.90(d, 1H), 6.96(d, 1H), 7.12(dd, 1H), 7.45(dd, 1H).

EXAMPLE 39

Production of 6-cyano-2,2-dimethyl-4-{1,2-dihydro-2-oxo-4-(1-phenoxythiocarbonyloxy-3-t-butyldimethylsilyloxypropyl)-1-pyridinyl}-2H-benzo[b]pyran.

In 30 ml of anhydrous acetonitrile, is dissolved 1.46 g of 6-cyano-2,2-dimethyl-4-{2-oxo-4-(1-hydroxy-3-t-butyldimethylsilyloxypropyl)-1-pyridinyl}-2H-benzo[b]pyran obtained in Example 38. Then, 0.73 g of 4-dimethylaminopyridine and 0.79 ml of phenoxythiocarbonyl chloride are added at room temperature, and reacted at that temperature for 6 hours. After stopping the reaction by adding 0.1M aqueous solution of sodium hydrogen carbonate, the reaction mixture is extracted with ether. The organic layer is washed successively with water and saturated aqueous solution of sodium chloride and dried over anhydrous sodium sulfate. The inorganic matter is filtered off and the filtrate is concentrated under reduced pressure. The residue is purified by silica gel column chromatography using ½ mixture of ethyl acetate/n-hexane as a developing solvent. Thus, 1.20 g of 6-cyano-2,2-dimethyl-4-{1,2-dihydro-2-oxo-4-(1-phenoxythiocarbonyloxy-3-t-butyldimethylsilyloxypropyl)-1-pyridinyl}-2H-benzo[b]pyran is obtained.

$^1$H-NMR (200 MHz, CDCl$_3$) δ:0.11(s, 6H), 0.94(s, 9H), 1.57(s, 3H), 1.62(s, 3H), 2.02–2.35(m, 2H), 3.69–3.94(m, 2H), 5.82(s, 1H), 6.19(m, 1H), 6.30(ddd, 1H), 6.68(s, 1H), 6.91(d, 1H), 6.99(t, 1H), 7.10(s, 1H), 7.14(s, 1H), 7.18(d, 1H), 7.32(d, 1H), 7.40(s, 1H), 7.43(s, 1H), 7.46(dd, 1H).

EXAMPLE 40

Production of 6-cyano-2,2-dimethyl-4-{1,2-dihydro-2-oxo-4-(3-t-butyldimethylsilyloxypropyl)-1-pyridinyl}-2H-benzo[b]pyran.

In 40 ml of anhydrous toluene, is dissolved 1.20 g of 6-cyano-2,2-dimethyl-4-{1,2-dihydro-2-oxo-4-(1-phenoxythiocarbonyloxy-3-t-butyldimethylsilyloxypropyl)-1-pyridinyl}-2H-benzo[b]pyran obtained in Example 39. Then, 0.66 g of 2,2'-azobisisobutyronitrile and 1.16 g of tri-n-butyltin hydride are added at room temperature and reacted at 100° C. for 30 minutes. After the reaction, the reaction mixture is directly purified by silica gel column chromatography using 1/1 mixture of ethyl acetate/n-hexane as a developing solvent. Thus, 0.83 g of 6-cyano-2,2-dimethyl-4-{1,2-dihydro-2-oxo-4-(3-t-butyldimethylsilyloxypropyl)-1-pyridinyl}-2H-benzo[b]pyran is obtained.

$^1$H-NMR (200 MHz, CDCl$_3$) δ:0.08(s, 6H), 0.92(s, 9H), 1.56(s, 3H), 1.62(s, 3H), 1.77–1.94(m, 2H), 2.60(t, 2H), 3.70(t, 2H), 5.78(s, 1H), 6.16(dd, 1H), 6.47(s, 1H), 6.89(d, 1H), 6.96(d, 1H), 7.05(d, 1H), 7.44(dd, 1H).

EXAMPLE 41

Production of 6-cyano-2,2-dimethyl-4-{1,2-dihydro-2-oxo-4-(3-hydroxypropyl)-1-pyridinyl}-2H-benzo[b]pyran.

In 7.50 ml of methanol, is dissolved 819 mg of 6-cyano-2,2-dimethyl-4-{2-oxo-4-(3-t-butyldimethylsilyloxypropyl)-1-pyridinyl}-2H-benzo[b]pyran obtained in Example 40. Then, 1.90 ml of 4N hydrochloric acid in dioxane is added thereto at 0° C., and reacted at room temperature for 30 minutes. The reaction mixture is concentrated under reduced pressure, the residue is mixed with ethyl acetate and water, and the product is extracted into ethyl acetate. The organic layer is washed with saturated aqueous solution of sodium chloride and dried over anhydrous sodium sulfate. The inorganic matter is filtered off, and the filtrate is concentrated under reduced pressure. The residue is purified by silica gel column chromatography using 1/10 mixture of methanol/methylene chloride as a developing solvent. Thus, 577 mg of 6-cyano-2,2-dimethyl-4-{1,2-dihydro-2-oxo-4-(3-hydroxypropyl)-1-pyridinyl}-2H-benzo[b]pyran is obtained.

EXAMPLE 42

Production of 6-cyano-2,2-dimethyl-4-{1,2-dihydro-2-oxo-4-(1,3-bismethanesulfonyloxypropyl)-1-pyridinyl}-2H-benzo[b]pyran In 8 ml of pyridine, is dissolved 0.71 g of 6-cyano-2,2-dimethyl-4-{1,2-dihydro-2-oxo-4-(1,3-dihydroxypropyl)-1-pyridinyl}-2H-benzo[b]pyran obtained in Example 37. Then, 8 ml of a solution containing 1.05 g of methanesulfonic acid anhydride in anhydrous methylene chloride is added to the solution at 0° C. and reacted at that temperature for one hour. After stopping the reaction by adding water, the reaction mixture is extracted with methylene chloride. The organic layer is washed successively with 2N aqueous hydrochloric acid, water and saturated aqueous solution of sodium chloride, and dried over anhydrous magnesium sulfate. The inorganic matter is filtered off and the filtrate is concentrated under reduced pressure. Thus, 1.03 g of 6-cyano-2,2-dimethyl-4-{1,2-dihydro-2-oxo-4-(1,3-bismethanesulfonyloxypropyl)-1-pyridinyl}-2H-benzo[b]pyran is obtained.

$^1$H-NMR (200 MHz, CDCl$_3$) δ:1.57(s, 3H), 1.61(s, 3H), 2.30–2.45(m, 2H), 3.11(s, 3H), 3.12(s, 3H), 4.43(t, 2H), 5.61(t, 1H), 5.82(d, 1H), 6.29(ddd, 1H), 6.68(dd, 1H), 6.92(d, 1H), 6.96(d, 1H), 7.23(dd, 1H), 7.46(dd, 1H).

EXAMPLE 43 (COMPOUND NO. 91)

Production of 6-cyano-2,2-dimethyl-4-{1,2-dihydro-2-oxo-4-(1,3-dinitroxypropyl)-1-pyridinyl}-2H-benzo[b]pyran In 12 ml of anhydrous toluene, is dissolved 1.03 g of 6-cyano-2,2-dimethyl-4-{1,2-dihydro-2-oxo-4-(1,3-bismethanesulfonyloxypropyl)-1-pyridinyl}-2H-benzo[b]pyran obtained in Example 35. Then, 5.48 g of tetra-n-butylammonium nitrate is added to the solution at room temperature and reacted at 90° C. for 4 hours. After stopping the reaction by adding ice water, the reaction mixture is extracted with ethyl acetate. The organic layer is washed successively with water and saturated aqueous solution of sodium chloride and dried over anhydrous sodium sulfate. The inorganic matter is filtered off and the filtrate is concentrated under reduced pressure. The residue is purified by silica gel column chromatography using 1/20 mixture of ethyl acetate/methylene chloride. Thus, 0.15 g of 6-cyano-2,2-dimethyl-4-{1,2-dihydro-2-oxo-4-(1,3-dinitroxypropyl)-1-pyridinyl}-2H-benzo[b]pyran is obtained.

$^1$H-NMR (200 MHz, CDCl$_3$) δ:1.57(s, 3H), 1.61(s, 3H), 2.23-2.45(m, 2H), 4.54-4.74(m, 2H), 5.68-5.80(m, 1H), 5.82(s, 1H), 6.25(ddd, 1H), 6.67(s, 1H), 6.92(d, 1H), 6.96(d, 1H), 7.22(s, 1H), 7.47(dd, 1H).

IR (KBr) cm$^{-1}$. 2310, 1670, 1640, 1600, 1275.

EXAMPLE 44

Production of 6-cyano-2,2-dimethyl-4-{1,2-dihydro-2-oxo-4-(1-hydroxy-4-p-methoxybenzyloxybutyl)-1-pyridinyl}-2H-benzo[b]pyran.

Forty milliliters of an anhydrous tetrahydrofuran solution containing 1.53 g of 6-cyano-2,2-dimethyl-4-(1,2-dihydro-2-oxo-4-formyl-1-pyridinyl)-2H-benzo[b]pyran, obtained in Example 25, is added at 0° C. to a Grignard reagent solution prepared from 0.19 g of magnesium and 1.94 g of 1-bromo-3-p-methoxybenzyloxy propane in 5 ml anhydrous tetrahydrofuran, and the resulting mixture is reacted first at that temperature for 10 minutes and then at room temperature for one hour. After stopping the reaction by adding a saturated aqueous solution of ammonium chloride, the reaction mixture is extracted with ethyl acetate. The organic layer is washed with saturated aqueous solution of sodium chloride and dried over anhydrous sodium sulfate. The inorganic matter is filtered off and the filtrate is concentrated under reduced pressure. The residue is purified by silica gel column chromatography using 1/1 mixture of ethyl acetate/methylene chloride as a developing solvent. Thus, 1.43 g of 6-cyano-2,2-dimethyl-4-{1,2-dihydro-2-oxo-4-(1-hydroxy-4-p-methoxybenzyloxybutyl)-1-pyridinyl}-2H-benzo[b]pyran is obtained.

$^1$H-NMR (200 MHz, CDCl$_3$) δ:1.56(s, 3H), 1.61(s, 3H), 1.75-1.88(m, 4H), 1.92(m, 1H), 3.55(t, 2H), 3.81(s, 3H), 4.50(s, 2H), 4.52-4.63(m, 1H), 5.78(d, 1H), 6.31(dt, 1H), 6.62(s, 1H), 6.90(d, 1H), 6.90(d, 2H), 6.93(dd, 1H), 7.10(d, 1H), 7.28(d, 2H), 7.44(dd, 1H).

EXAMPLE 45

Production of 6-cyano-2,2-dimethyl-4-{1,2-dihydro-2-oxo-4-(1-phenoxythiocarbonyloxy-4-p-methoxybenzyloxybutyl)-1-pyridinyl}-2H-benzo[b]pyran.

In 30 ml of anhydrous acetonitrile, is dissolved 1.42 g of 6-cyano-2,2-dimethyl-4-{1,2-dihydro-2-oxo-4-(1-hydroxy-4-p-methoxybenzyloxybutyl)-1-pyridinyl}-2H-benzo[b]pyran obtained in Example 44. Then, 1.50 g of 4-dimethylaminopyridine and 0.81 ml of phenoxythiocarbonyl chloride are added to the solution at room temperature, and reacted at that temperature for 8 hours. After stopping the reaction by adding 0.1M aqueous solution of sodium hydrogen carbonate, the reaction mixture is extracted with ether. The organic layer is washed successively with water and saturated aqueous solution of sodium chloride and dried over anhydrous sodium sulfate. The inorganic matter is filtered off and the filtrate is concentrated under reduced pressure. The residue thus obtained is purified by silica gel column chromatography using ½ mixture of ethyl acetate/n-hexane as a developing solvent. Thus, 1.61 g of 6-cyano-2,2-dimethyl-4-{1,2-dihydro-2-oxo-4-(1-phenoxythiocarbonyloxy-4-p-methoxybenzyloxybutyl)-1-pyridinyl}-2H-benzo[b]pyran is obtained.

$^1$H-NMR (200 MHz, CDCl$_3$) δ:1.56(s, 3H), 1.61(s, 3H), 1.72-1.89(m, 2H), 2.06-2.22(m, 2H), 3.54(t, 2H), 3.80(s, 3H), 4.46(s, 2H), 5.81(s, 1H), 6.09(dd, 1H), 6.26(dd, 1H), 6.65(s, 1H), 6.86-6.94(m, 3H), 6.98(t, 1H), 7.08-7.18(m, 3H), 7.28-7.35(m, 2H), 7.38-7.49(m, 4H).

EXAMPLE 46

Production of 6-cyano-2,2-dimethyl-4-{1,2-dihydro-2-oxo-4-(4-p-methoxybenzyloxybutyl)-1-pyridinyl}-2H-benzo[b]pyran.

In 46 ml of anhydrous toluene, is dissolved 1.44 g of 6-cyano-2,2-dimethyl-4-(1,2-dihydro-2-oxo-4-(1-phenoxythiocarbonyloxy-4-p-methoxybenzyloxybutyl)-1-pyridinyl}-2H-benzo[b]pyran obtained in Example 45. Then, 0.76 g of 2,2'-azobisisobutyronitrile and 1.35 g of tri-n-butyltin hydride are added and reacted at 100° C. for 15 minutes. After the reaction, the reaction mixture is directly purified by silica gel column chromatography using 3/2 mixture of ethyl acetate/n-hexane as a developing solvent. Thus, 1.03 g of 6-cyano-2,2-dimethyl-4-{1,2-dihydro-2-oxo-4-(4-p-methoxybenzyloxybutyl)-1pyridinyl-}-2H-benzo[b]pyran is obtained.

$^1$H-NMR (200 MHz, CDCl$_3$) δ:1.56(s, 3H), 1.61(s, 3H), 1.67-1.78(m, 4H), 2.52(t, 2H), 3.50(t, 2H), 3.81(s, 3H), 4.45(s, 2H), 5.78(s, 1H), 6.13(dd, 1H), 6.45(d, 1H), 6.89(d, 1H), 6.89(d, 2H), 6.96(d, 1H), 7.04(d, 1H), 7.28(d, 2H), 7.44(dd, 1H).

EXAMPLE 47

Production of 6-cyano-2,2-dimethyl-4-{1,2-dihydro-2-oxo-4-(4-hydroxybutyl)-1-pyridinyl}-2H-benzo[b]pyran In 24 ml of methylene chloride, is dissolved 1.13 g of 6-cyano-2,2-dimethyl-4-{2-oxo-4-(4-p-methoxybenzyloxybutyl)-1-pyridinyl}-2H-benzo[b]pyran obtained in Example 46. Then, 1.33 ml of water is added. Then, 0.82 g of 2,3-dichloro-5,6-dicyano-1,4-benzoquinone is added at room temperature and the resulting mixture is reacted at that temperature for 40 minutes. After stopping the reaction by adding water, the reaction mixture is extracted with methylene chloride. The organic layer is washed successively with 0.1M aqueous solution of sodium hydrogen carbonate and saturated aqueous solution of sodium chloride and dried over anhydrous sodium sulfate. The inorganic matter is filtered off and the filtrate is concentrated under reduced pressure. The residue is purified by silica gel column chromatography using 1/10 mixture of methanol/methylene chloride as a developing solvent. Thus, 0.78 g of 6-cyano-2,2-dimethyl-4-{1,2-dihydro-2-oxo-4-(4-hydroxybutyl)-1-pyridinyl}-2H-benzo[b]pyran is obtained.

$^1$H-NMR (200 MHz, CDCl$_3$) δ:1.56(s, 3H), 1.61(s, 3H), 1.65-1.77(m, 5H), 2.56(t, 2H), 3.71(t, 2H), 5.79(s, 1H), 6.16(dd, 1H), 6.47(s, 1H), 6.90(d, 1H), 6.96(d, 1H), 7.06(d, 1H), 7.44(dd, 1H).

EXAMPLE 48

Production of 6-cyano-2,2-dimethyl-4-{1,2-dihydro-2-oxo-4-(4-methanesulfonyloxybutyl)-1-pyridinyl}- 2H-benzo[b]pyran.

In 6 ml of pyridine, is dissolved 631 mg of 6-cyano-2,2-dimethyl-4-{2-oxo-4-(4-hydroxybutyl)-1-pyridinyl}-2H-benzo[b]pyran obtained in Example 47. Then, 6 ml of a solution containing 470 mg of methanesulfonic acid anhydride in anhydrous methylene chloride is dropped into the solution at 0° C., and reacted at that temperature for 30 minutes. After stopping the reaction by adding water, the reaction mixture is extracted with methylene chloride. The organic layer is washed successively with 2N aqueous hydrochloric acid, water and saturated aqueous solution of sodium chloride, and dried over anhydrous magnesium sulfate. The inorganic matter is filtered off, and the filtrate is concentrated under reduced pressure to obtain 765 mg of 6-cyano-2,2-dimethyl-4-{1,2-dihydro-2-oxo-4-(4-methanesulfonyloxybutyl)-1-pyridinyl}-2H-benzo[b]pyran.

1H-NMR 1H-NMR (200 MHz, CDCl$_3$) δ:1.56(s, 2H), 1.62(s, 2H), 1.78-1.90(m, 4H), 2.58(t, 2H), 3.04(s, 3H), 4.29(t, 2H), 5.80(s, 1H), 6.15(dd, 1H), 6.46(d, 1H), 6.90(d, 1H), 6.96(d, 1H), 7.08(d, 1H), 7.45(dd, 1H).

EXAMPLE 49 (COMPOUND NO. 81)

Production of 6-cyano-2,2-dimethyl-4-{1,2-dihydro-2-oxo-4-(4-nitroxybutyl)-1-pyridinyl}-2H-benzo[b]pyran In 72 ml of anhydrous toluene, is dissolved 0.77 g of 6-cyano-2,2-dimethyl-4-{1,2-dihydro-2-oxo-4-(4-methanesulfonyloxybutyl)- 1-pyridinyl}-2H-benzo[b]pyran obtained in Example 48. Then, 1.64 g of tetra-n-butylammonium nitrate is added to the solution at room temperature and reacted at 90° C. for one hour. After stopping the reaction by adding ice water, the reaction mixture is extracted with ethyl acetate. The organic layer is washed successively with water and saturated aqueous solution of sodium chloride and dried over anhydrous sodium sulfate. The inorganic matter is filtered off, and the filtrate is concentrated under reduced pressure. The residue is purified by silica gel column chromatography using ¼ mixture of ethyl acetate/-methylene chloride to obtain 0.65 g of 6-cyano-2,2-dimethyl-4-{1,2-dihydro-2-oxo-4-(4-nitroxybutyl)-1pyridinyl}-2H-benzo[b]pyran.

1H-NMR 1H-NMR (200 MHz, CDCl$_3$) δ:1.56(s, 3H), 1.62(s, 3H), 1.72-1.90(m, 4H), 2.57(t, 2H), 4.51(t, 2H), 5.79(s, 1H), 6.13(dd, 1H), 6.46(s, 1H), 6.90(d, 1H), 6.95(d, 1H), 7.08(d, 1H), 7.45(dd, 1H).

IR (KBr) cm$^{-1}$. 2310, 1670, 1635, 1600, 1280.

EXAMPLE 50 (COMPOUND NO. 187)

Production of trans-3-hydroxy-6-trifluoromethyl-3,4-dihydro-2,2-dimethyl-4-(1,2-dihydro-2-oxo-4-t-butyldimethylsilyloxymethyl-1-pyridinyl)-2H-benzo[b]pyran The reaction and after treatment of Example 1 are repeated, except that the 3,4-epoxy-3,4-dihydro-6-cyano-2,2-dimethyl-2H-benzo[b]pyran used in Example 1 is replaced with 3,4-epoxy-3,4-dihydro-6-trifluoromethyl-2,2-dimethyl-2H-benzo[b]pyran. Thus, trans-3-hydroxy-6-trifluoromethyl-3,4-dihydro-2,2-dimethyl-4-(1,2-dihydro-2-oxo-4-t-butyldimethylsilyloxymethyl-1-pyridinyl)-2H-benzo[b]pyran is obtained.

1H-NMR 1H-NMR (200 MHz, CDCl$_3$) δ:0.12(s, 6H), 0.95(s, 9H), 1.35(s, 3H), 1.54(s, 3H), 3.85(d, 1H), 4.22(br, 1H), 4.58(s, 2H), 6.17(dd, 1H), 6.33(d, 1H). 6.71(m, 1H), 6.85(d, 1H), 7.01(m, 2H), 7.47(dd, 1H)

EXAMPLE 51 (COMPOUND NO. 188)

Production of 6-trifluoromethyl-2,2-dimethyl-4-(1,2-dihydro-2-oxo-4-t-butyldimethylsilyloxymethyl-1-pyridinyl)-2H-benzo[b]pyran.

The reaction and after treatment of Example 8 are repeated, except that the trans-3-hydroxy-6-cyano-3,4-dihydro-2,2-dimethyl-4-(1,2-dihydro-2-oxo-4-t-butyldimethylsilyloxymethyl-1-pyridinyl)-2H-benzo[b]pyran used in Example 8 is replaced with the trans-3-hydroxy-6-trifluoromethyl-3,4-dihydro-2,2-dimethyl-4-(1,2-dihydro-2-oxo-4-t-butyldimethylsilyloxymethyl-1-pyridinyl)-2H-benzo[b]pyran obtained in Example 50. Thus, 6-trifluoromethyl-2,2-dimethyl-4-(1,2-dihydro-2-oxo-4-t-butyldimethylsilyloxymethyl-1-pyridinyl)-2H-benzo[b]pyran is obtained.

1H-NMR 1H-NMR (200 MHz, CDCl$_3$) δ:0.14(s, 6H), 0.96(s, 9H), 1.55(s, 3H), 1.61(s, 3H), 4.61(d, 2H), 5.76(s, 1H), 6.19(dd, 1H), 6.64(s, 1H), 6.92(d, 2H), 7.10(d, 1H), 7.41(dd, 1H).

EXAMPLE 52 (COMPOUND NO. 189)

Production of 6-trifluoromethyl-2,2-dimethyl-4-(1,2-dihydro-2-oxo-4-hydroxymethyl-1-pyridinyl)-2H-benzo[b]pyran The reaction and after treatment of Example 9 are repeated, except that the 6-cyano-2,2-dimethyl-4-(1,2-dihydro-2-oxo-4-t-butyldimethylsilyloxymethyl-1-pyridinyl)-2H-benzo[b]pyran used in Example 9 is replaced with the 6-trifluoromethyl-2,2-dimethyl-4-(1,2-dihydro-2-oxo-4-t-butyldimethylsilyloxymethyl-1-pyridinyl)-2H-benzo[b]pyran obtained in Example 51. Thus, 6-trifluoromethyl-2,2-dimethyl-4-(1,2-dihydro-2-oxo-4-hydroxymethyl-1-pyridinyl)-2H-benzo[b]pyran (Compound No. 189) is obtained.

1H-NMR 1H-NMR (200 MHz, CDCl$_3$) δ:1.55(s, 3H), 1.61(s, 3H), 3.10(br, 1H), 4.57(s, 2H), 5.77(s, 1H), 6.24(dd, 1H), 6.68(s, 1H), 6.89(m, 2H), 7.13(d, 1H), 7.42(dd, 1H).

EXAMPLE 53 (COMPOUND NO. 105)

Production of 6-trifluoromethyl-2,2-dimethyl-4-(1,2-dihydro-2-oxo-4-nitroxymethyl-1-pyridinyl)-2H-benzo[b]pyran The reaction and after treatment of Examples 10 and 11 are repeated, except that the 6-cyano-2,2-dimethyl-4-(1,2-dihydro-2-oxo-4-hydroxymethyl-1-pyridinyl)-2H-benzo[b]pyran used in Example 10 is replaced with the 6-trifluoromethyl-2,2-dimethyl-4-(1,2-dihydro-2-oxo-4-hydroxymethyl-1-pyridinyl)-2H-benzo[b]pyran obtained in Example 52. Thus, 6-trifluoromethyl-2,2-dimethyl-4-(1,2-dihydro-2-oxo-4-nitroxymethyl-1-pyridinyl)-2H-benzo[b]pyran (Compound No. 105) is obtained.

1H-NMR 1H-NMR (200 MHz, CDCl$_3$) δ:1.56(s, 3H), 1.58(s, 3H), 5.33(s, 2H), 5.79(s, 1H), 6.24(dd, 1H), 6.75(s, 1H), 6.91(m, 2H), 7.21(d, 1H), 7.43(dd, 1H).

IR (KBr) cm$^{-1}$. 1660, 1645, 1590, 1305, 1275.

What is claimed is:

1. A chroman derivative represented by the following general formula (I):

wherein $R_1$ represents cyano group, nitro group, halogenomethyl group or —SO$_2$—X group (X represents lower alkyl group having 1–6 carbon atoms or aryl group); $R_2$ represents hydrogen atom or OA group (A represents hydrogen atom, nitro group, lower acyl group having 1–6 carbon atoms, arylcarbonyl group, lower alkylsulfonyl group having 1–6 carbon atoms, arylsulfonyl group, arylalkyl group, tetrahydropyranyl group, lower alkoxycarbonyl group having 1-6 carbon atoms, arylalkoxycarbonyl group or silyl derivative group); $R_3$ singly represents a hydrogen atom; or $R_2$ forms a bond jointly with $R_3$; and at least one of $R_4$, $R_5$, $R_6$ and $R_7$ represents —Y—$(ONO_2)_n$ and the remaining represent a hydrogen atom (Y represents straight or branched chain alkylene group having 1-6 carbon atoms or lower alkenylene group having 1-6 carbon atoms, and n represents an integer of 1-3.

2. A chroman derivative according to claim 1, wherein $R_1$ is cyano group or halogenomethyl group, $R_2$ is hydroxyl group or acetoxy group, $R_3$ singly represents a hydrogen atom, or $R_3$ forms a bond jointly with $R_2$, any one of $R_4$, $R_5$ and $R_6$ is —Y—$(ONO_2)_n$ group and the other two are each a hydrogen atom, and $R_7$ is a hydrogen atom.

3. A chroman derivative accordingly to claim 2, wherein $R_1$ is cyano group or trifluoromethyl group, $R_2$ and $R_3$ jointly form a bond, and $R_5$ is —Y—$(ONO_2)_n$ group.

4. A chroman derivative according to claim 3, wherein Y is $C_{1-4}$(poly)methylene group optionally having methyl group, and n is 1.

5. 6-Cyano-2,2-dimethyl-4-(1,2-dihydro-2-oxo-4-nitroxymethyl-1-pyridinyl)-2H-benzo[b]pyran.

6. 6-Cyano-2,2-dimethyl-4-{1,2-dihydro-2-oxo-4-(1-nitroxyethyl)-1-pyridinyl}-2H-benzo[b]pyran.

7. 6-Cyano-2,2-dimethyl-4-{1,2-dihydro-2-oxo-4-(3-nitroxypropyl)-1-pyridinyl}-2H-benzo[b]pyran.

8. 6-Trifluoromethyl-2,2-dimethyl-4-(1,2-dihydro-2-oxo-4-nitroxymethyl-1-pyridinyl)-2H-benzo[b]pyran.

9. A method for treating the symptoms caused by contraction of smooth muscles, the diseases of the circulatory system or epilepsy which comprises administering to mannals an effective quantity of a chroman derivative represented by general formula (1):

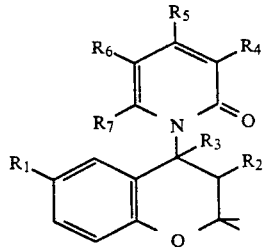
(1)

wherein $R_1$ represents cyano group, nitro group, halogenomethyl group or —$SO_2$—X group (X represents lower alkyl group having 1-6 carbon atoms or aryl group); $R_2$ represents hydrogen atom or OA group (A represents hydrogen atom, nitro group, lower acyl group having 1-6 carbon atoms, arylcarbonyl group, lower alkylsulfonyl group having 1-6 carbon atoms, arylsulfonyl group, arylalkyl group, tetrahydropyranyl group, lower alkoxycarbony group having 1-6 carbon atoms, arylalkoxycarbonyl group or silyl derivative group); $R_3$ singly represents a hydrogen atom; or $R_3$ forms a bond jointly with $R_2$; and at least one of $R_4$, $R_5$, $R_6$ and $R_7$ represents —Y—$(ONO_2)_n$ and the remaining represent a hydrogen atom (Y represents straight or branched chain alkylene group having 1-6 carbon atoms or lower alkenylene group having 1-6 carbon atoms, and n represents an integer of 1-3.

10. A method according to claim 9, wherein the compound of formula (1) is 6-cyano-2,2-dimethyl-4-(1,2-dihydro-2-oxo-4-nitroxymethyl-1-pyridinyl)-2H-benzo[b]pyran, 6-cyano-2,2-dimethyl-4-{1,2-dihydro-2-oxo-4-(1-nitroxyethyl)-1-pyridinyl}-2H-benzo[b]pyran, 6-cyano-2,2-dimethyl-4-{1,2-dihydro-2-oxo-4-(3-nitroxypropyl)-1-pyridinyl}-2H-benzo[b]pyran or 6-trifluoromethyl-2,2-dimethyl-4-(1,2-dihydro-2-oxo-4-nitroxymethyl-1-pyridinyl)-2H-benzo[b]pyran, the disease of the circulatory system is angina pectoris, hypertension, cardiac insufficiency, myocardial infarction, myocardial injury or arrhythmia, the symptoms caused by contraction of smooth muscles is asthma or dysuria.

11. A pharmaceutical composition comprising 0.01-99% chroman derivative represented by the following formula (1) and 1-99.99% of additives:

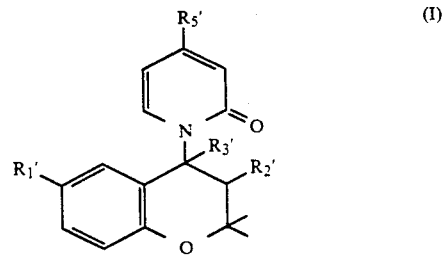
(I)

wherein $R_1$ represents cyano group, nitro group, halogenomethyl group or —$SO_2$—X group (X represents lower alkyl group having 1-6 carbon atoms or aryl group); $R_2$ represents hydrogen atom or OA group (A represents hydrogen atom, nitro group, lower acyl group having 1-6 carbon atoms, arylcarbonyl group, lower alkylsulfonyl group having 1-6 carbon atoms, arylsulfonyl group, arylalky group, tetrahydropyranyl group, lower alkoxycarbonyl group having 1-6 carbon atoms, arylalkoxycarbonyl group or silyl derivative group): $R_3$ singly represents a hydrogen atom; or $R_3$ forms a bond jointly with $R_2$; and at least one $R_4$, $R_5$, $R_6$ and $R_7$ represents —Y—$(ONO_2)_n$ and the remaining represent a hydrogen atom (Y represents straight or branched chain alkylene group having 1-6 carbon atoms or lower alkenylene group having 1-6 carbon atoms, and n represents an integer of 1-3.

12. A composition according to claim 11, wherein the compound of formula is 6-cyano-2,2-dimethyl-4-(1,2-dihydro-2-oxo-4-nitroxymethyl-1-pyridinyl)-2H-benzo[b]pyran, 6-cyano-2,2-dimethyl-4-{1,2-dihydro-2-oxo-4-(1-nitroxyethyl)-1-pyridinyl}-2H-benzo[b]pyran, 6-cyano-2,2-dimethyl-4-{1,2-dihydro-2-oxo-4-(3-nitroxypropyl)- 1-pyridinyl}-2H-benzo[b]pyran or 6-trifluoromethyl-2,2-dimethyl-4-(1,2-dihydro-2-oxo-4-nitroxymethyl-1-pyridinyl)-2H-benzo[b]pyran.

* * * * *